(12) United States Patent      (10) Patent No.: US 7,504,397 B2
Hummersone et al.      (45) Date of Patent: Mar. 17, 2009

(54) MTOR INHIBITOR COMPOUNDS

(75) Inventors: Marc Geoffrey Hummersone, Cambridge (GB); Sylvie Gomez, Cambridge (GB); Keith Allan Menear, Cambridge (GB); Xiao-Ling Fan Cockcroft, Cambridge (GB); Graeme Cameron Murray Smith, Cambridge (GB)

(73) Assignee: Kudos Pharmaceuticals Ltd., Cambridge (GB)

( * ) Notice: Subject to any disclaimer, the term of this patent is extended or adjusted under 35 U.S.C. 154(b) by 293 days.

(21) Appl. No.: 11/361,599

(22) Filed: Feb. 24, 2006

(65) Prior Publication Data

US 2006/0199804 A1    Sep. 7, 2006

Related U.S. Application Data

(60) Provisional application No. 60/656,193, filed on Feb. 25, 2005.

(30) Foreign Application Priority Data

Feb. 25, 2005    (GB)   ................................. 0503962.3

(51) Int. Cl.
    *A01N 43/58*      (2006.01)
    *A61K 31/50*      (2006.01)
    *C07D 239/00*    (2006.01)
    *C07D 239/02*    (2006.01)

(52) U.S. Cl. ........................................ 514/247; 544/242
(58) Field of Classification Search ........................ None
See application file for complete search history.

(56) References Cited

U.S. PATENT DOCUMENTS

| 4,766,213 A | 8/1988 | Juraszyk et al. |
|---|---|---|
| 6,335,339 B1 | 1/2002 | Arenas et al. |

FOREIGN PATENT DOCUMENTS

| WO | WO 01/68611 | | 9/2001 |
|---|---|---|---|
| WO | WO 02/089809 | | 11/2002 |
| WO | WO 03/022833 | * | 3/2003 |
| WO | WO 2005/028467 | | 3/2005 |

OTHER PUBLICATIONS

Vippagunta et al. Advanced Drug Delivery Reviews, 2001, 48, 3-26.*
Stella, V. Expert Opinions in Therapeutic Patents, 2004, 14(3), 277-80.*
Greene et al. Protective Groups in Organic Synthesis, 1999, pp. 17-23 and 494-503.*
Abraham, R.T., "Phosphatidylinositol 3-kinase related kinases," Curr. Opin. Immun. (1996) 8:412-418.
Berge, S.M. et al., "Pharmaceutical Salts," J. Pharm. Sci. (1977) 66(1):1-19.
Bjornsti, M-A. et al., "The TOR pathway: a target for cancer therapy," Nat. Rev. Cancer (2004) 4:335-348.
Brown, E.J. et al., "A mammalian protein targeted by G1-arresting rapamycin-receptor complex," Nature (1994) 369:756-758.
Brunn, G.J. et al., "Direct inhibition of the signaling functions of the mammalian target of rapamycin by the phosphoinositide 3-kinase inhibitors, wortmannin and LY294002," EMBO J. (1996) 15(19):5256-5267.
Burnett, P.E. et al., "RAFT1 phosphorylation of the translational regulators p70 S6 kinase and 4E-BP1," Proc. Natl. Acad. Sci. USA (1998) 95:1432-1437.
Chiu, M.I. et al., "RAPT1, a mammalian homolog of yeast Tor, interacts with the FKBP12/rapamycin complex," Proc. Natl. Acad. Sci. USA (1994) 91:12574-12578.
Dahia, P.L.M., "PTEN, a unique tumor suppressor gene," Endocrine-Rel. Cancer (2000) 7:115-129.
Di Cristofano, A. et al., "The multiple roles of PTEN in tumor suppression," Cell (2000) 100:387-390.
Edinger, A.L. et al., "Differential effects of rapamycin on mammalian target of rapamycin signaling functions in mammalian cells," Cancer Res. (2003) 63:8451-8460.
Eshleman, J.S. et al., "Inhibition of the mammalian target of rapamycin sensitizes U87 xenografts to fractionated radiation therapy," Cancer Res. (2002) 62:7291-7297.
Gingras, A-C. et al., "Regulation of 4E-BP1 phosphorylation: a novel two-step mechanism," Gene & Dev. (1999) 13:1422-1437.
Gingras, A-C. et al., "Regulation of translation initiation by FRAP/mTOR," Genes & Dev. (2001) 15:807-826.
Huang, S. et al., "Inhibitors of mammalian target of rapamycin as novel antitumor agents: from bench to clinic," Curr. Opin. Invest. Drugs (2002) 3(2):295-304.
Huang, S. et al., "Targeting mTOR signaling for cancer therapy," Curr. Opin. Pharma. (2003) 3:371-377.
Jefferies, H.B.J. et al., "Rapamycin suppresses 5'TOP mRNA translation through inhibition of $p70^{s6k}$," EMBO J. (1997) 16(12):3693-3704.
Lawrence, J.C. et al., "Modulation of the protein kinase activity of mTOR," Curr. Top Microbiol. Immunol. (2003) 279:199-213.
Neuhaus, P. et al., "mTOR inhibitors: an overview," Liver Transplantation (2001) 7(6):473-484.
Sabatini, D.M. et al., "RAFT1: a mammalian protein that binds to FKBP12 in a rapamycin-dependent fashion and is homologous to yeast TORs," Cell (1994) 78:35-43.
Sabers, C.J. et al., "Isolation of a protein target of the RKBP12-rapamycin complex in mammalian cells," J. Biol. Chem. (1995) 270(2):815-822.

(Continued)

*Primary Examiner*—James O Wilson
*Assistant Examiner*—Noble Jarrell
(74) *Attorney, Agent, or Firm*—Morgan, Lewis & Bockius LLP

(57) ABSTRACT

Compounds of formula I:

A-B-C                       (I)

and isomers, salts, solvates, chemically protected forms, and prodrugs thereof are provided, wherein variables A, B and C are defined herein and wherein such compounds act as mTor inhibitors.

14 Claims, No Drawings

OTHER PUBLICATIONS

Samuels, Y. et al., "High frequency of mutations of the PIK3CA gene in human cancers," Science (2004) 304:554.

Sawyers, C.L. et al., "Will mTOR inhibitors make it as cancer drugs?" Cancer Cell (2003) 4:343-348.

Schmelzle, T. et al., "TOR, a central controller of cell growth," Cell (2000) 103:253-262.

Terada, N. et al., "Rapamycin selectively inhibits translation of mRNAs encoding elongation factors and ribosomal proteins," Proc. Natl. Acad. Sci. USA (1994) 91:11477-11481.

Woods, T.C. et al., "Drug-eluting stents," Annu. Rev. Med. (2004) 55:169-178.

* cited by examiner

MTOR INHIBITOR COMPOUNDS

CROSS-REFERENCE TO RELATED APPLICATIONS

This application claims the priority benefit of U.S. Provisional Patent Application Ser. No. 60/656,193 filed on Feb. 25, 2005 and United Kingdom Patent Application No, 0503962.3 filed Feb. 25, 2005. These applications are incorporated herein by reference.

The present invention relates to compounds which act as mTOR inhibitors, their use and their synthesis.

BACKGROUND

Growth factor/mitogenic activation of the phosphatidylinositol 3-kinase (PI3K)/AKT signalling pathway ultimately leads to the key cell cycle and growth control regulator mTOR, the mammalian target of rapamycin (alternatively referred to as FRAP (FKBP12 and rapamycin associated protein), RAFT1 (rapamycin and FKBP12 target 1), RAPT1 (rapamycin target 1)—all derived from the interaction with the FK-506-binding protein FKBP12, and SEP (sirolimus effector protein)). mTOR is a mammalian serine/threonine kinase of approximately 289 kDa in size and a member of the evolutionary conserved eukaryotic TOR kinases (refs. 1-4). The mTOR protein is a member of the PI3-kinase like kinase (PIKK) family of proteins due to its C-terminal homology (catalytic domain) with PI3-kinase and the other family members, e.g. DNA-PKcs (DNA dependent protein kinase), ATM (Ataxia-telangiectasia mutated). In addition to a catalytic domain in the C-terminus, mTOR contains a FKBP12/rapamycin complex binding domain (FRB). At the N-terminus up to 20 HEAT (Huntingtin, EF3, alpha regulatory subunit of PP2A and TOR) motifs are found whilst more C-terminal is a FAT (FRAP-ATM-TRRAP) domain, and at the extreme C-terminus of the protein an additional FAT domain is found (FAT-C) (refs. 5,6).

TOR has been identified as a central regulator of both cell growth (size) and proliferation, which is in part governed by translation initiation. TOR dependant phosphorylation of S6-kinase (S6K1) allows translation of ribosomal proteins involved in cell cycle progression (refs. 7-9). Cap-dependant translation is regulated by the phosphorylation of the eukaryotic translation initiation factor 4E (eIF4E)-binding protein 1 (4E-BP1 (PHAS-1)). This modification prevents PHAS-1 binding eIF4E, thereby permitting formation of an active eIF4F translation complex (reviewed in refs. 10,11,12). Activation of these signalling elements is dependant on insulin, other growth factors and nutrients suggesting a gatekeeper role for mTOR in the control of cell cycle progression only under favourable environmental conditions. The PI3K/AKT signalling cascade lies upstream of mTOR and this has been shown to be deregulated in certain cancers and results in growth factor independent activation in, for example, PTEN deficient cells. mTOR lies at the axis of control for this pathway and inhibitors of this kinase (e.g. sirolimus (rapamycin or Rapamune™) and everolimus (RAD001 or Certican™)) are already approved for immunosuppression and drug eluting stents (reviewed in refs. 13, 14), and are now receiving particular interest as novel agents for cancer treatment.

Tumour cell growth arises from the deregulation of normal growth control mechanisms such as the loss of tumour suppressor function(s). One such tumour suppressor is the phosphatase and tensin homologue deleted from chromosome ten (PTEN). This gene, also known as mutated in multiple advanced cancers (MMAC), has been shown to play a significant role in cell cycle arrest and is the most highly mutated tumour suppressor after p53. Up to 30% of glioblastoma, endometrial and prostate cancers have somatic mutations or deletions of this locus (refs. 15, 16).

PI3K converts phosphatidylinositol 4,5, bisphosphate (PIP2) to phosphatidylinositol 3,4,5, triphosphate (PIP3) whilst PTEN is responsible for removing the 3' phosphate from PIP3 producing PIP2. PI3-K and PTEN act to maintain an appropriate level of PIP3 which recruits and thus activates AKT (also known as PKB) and the downstream signalling cascade that is then initiated. In the absence of PTEN, there is inappropriate regulation of this cascade, AKT becomes effectively constitutively activated and cell growth is deregulated. An alternative mechanism for the deregulation of this cell signalling process is the recent identification of a mutant form of the PI3K isoform, p110 alpha (ref. 17). The apparent increased activity of this mutant is thought to result in increased PIP3 production, presumably in excess of that which the function of PTEN can counteract. Increased signalling from PI3K, thus results in increased signalling to mTOR and consequently, its downstream activators.

In addition to the evidence linking mTOR with cell cycle regulation (from G1 to S-phase) and that inhibition of mTOR results in inhibition of these regulatory events it has been shown that down regulation of mote activity results in cell growth inhibition (Reviewed in refs. 7,18,19). The known inhibitor of mTOR, rapamycin, potently inhibits proliferation or growth of cells derived from a range of tissue types such as smooth muscle, T-cells as well as cells derived from a diverse range of tumour types including rhabdomyosarcoma, neuroblastoma, glioblastoma and medulloblastoma, small cell lung cancer, osteosarcoma, pancreatic carcinoma and breast and prostate carcinoma (reviewed in ref. 20).

Rapamycin has been approved and is in clinical use as an immunosuppressant, its prevention of organ rejection being successful and with fewer side effects than previous therapies (refs. 20, 21). Inhibition of mTOR by rapamycin and its analogues (RAD001, CCl-779) is brought about by the prior interaction of the drug with the FK506 binding protein, FKBP12. Subsequently, the complex of FKBP12/rapamycin then binds to the FRB domain of mTOR and inhibits the downstream signalling from mTOR.

The potent but non-specific inhibitors of PI3K, LY294002 and wortmannin, also have been shown to inhibit the kinase function of mTOR but act through targeting the catalytic domain of the protein (ref. 21). Further to the inhibition of mTOR function by small molecules targeted to the kinase domain, it has been demonstrated that kinase dead mTOR cannot transmit the upstream activating signals to the downstream effectors of mTOR, PHAS-1 or p70S6 kinase (ref. 22). It is also shown that not all functions of mTOR are rapamycin sensitive and this may be related to the observation that rapamycin alters the substrate profile of mTOR rather than inhibiting its activity per se (ref. 23). Therefore, it is proposed that a kinase domain directed inhibitor of mTOR may be a more effective inhibitor of mTOR.

In addition to rapamycin's ability to induce growth inhibition (cytostasis) in its own right, rapamycin and its derivatives have been shown to potentiate the cytotoxicity of a number of chemotherapies including cisplatin, camptothecin and doxorubicin (reviewed in ref. 20). Potentiation of ionising radiation induced cell killing has also been observed following inhibition of mTOR (ref. 24) Experimental and clinical evidence has shown that rapamycin analogues are showing evidence of efficacy in treating cancer, either alone or in combination with other therapies (see refs. 10,18,20).

The vast majority of mTOR pharmacology to date has focused on inhibition of mTOR via rapamycin or its analogues. However, as noted above, the only non-rapamycin agents that have been reported to inhibit mTOR's activity via a kinase domain targetted mechanism are the small molecule LY294002 and the natural product wortmannin (ref. 21).

SUMMARY OF THE INVENTION

The present inventors have identified compounds which are ATP-competitive inhibitors of mTOR, and hence are non-rapamycin like in their mechanism of action.

Accordingly, the first aspect of the present invention provides a compound of formula I:

A-B-C    (I)

and isomers, salts, solvates, chemically protected forms, and prodrugs thereof wherein:

B is selected from the group consisting of:

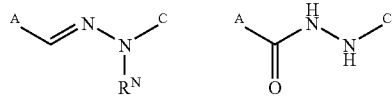

where $R^N$ is H or Me;
or B is a divalent $C_5$ heterocyclic residue containing one or two ring heteroatoms;

A is:

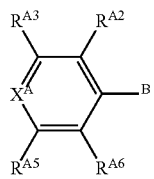

$R^{A3}$ and $R^{A5}$ are independently selected from halo, $OR^O$ and $R^{AC}$, where $R^O$ is H or Me, and $R^{AC}$ is H or $C_{1-4}$ alkyl;
$X^A$ is selected from N and $CR^{A4}$, where $R^{A4}$ is selected from H, $OR^O$, $CH_2OH$, $CO_2H$, $NHSO_2Me$ and $NHCOMe$;
$R^{A2}$ and $R^{A6}$ are independently selected from H, halo and $OR^O$;
or $R^{A3}$ and $R^{A4}$ together with the carbon atoms to which they are attached, or $R^{A2}$ and $R^{A3}$ together with the carbon atoms to which they are attached, may form a $C_{5-6}$ heterocylic or heteroaromatic ring, containing at least one nitrogen ring atom;
where if X is not N, 1, 2, or 3 of $R^{A2}$ to $R^{A6}$ are not H;

C is:

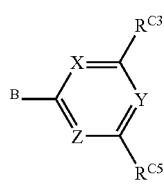

where X is selected from N and CH, Y is selected from N and CH, and Z is selected from N and $CR^{C6}$;

$R^{C3}$ is selected from H, halo and an optionally substituted N-containing $C_{5-7}$ heterocyclic group;
$R^{C5}$ is a group selected from:

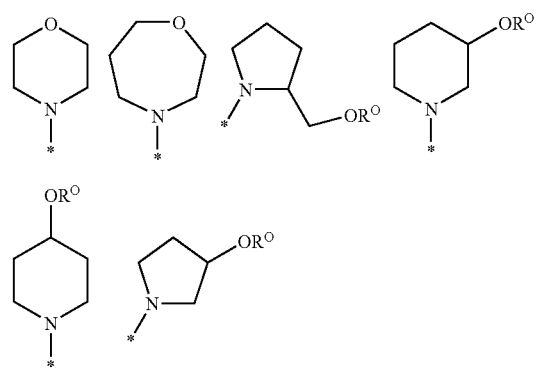

which group may be selected by one or two $C_{1-4}$ alkyl groups or a carboxy group;
$R^{C6}$ is H;
or, when X and Y are N, $R^{C5}$ and $R^{C6}$ (when Z is $CR^{C6}$) together with the carbon atoms to which they are attached may form a fused $C_6$ aromatic ring selected from the group consisting of:

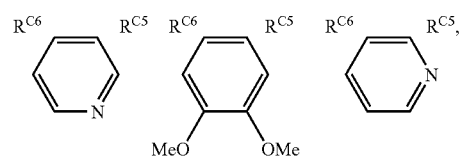

with the proviso that when X and Y are N and Z is N or CH, $R^{C3}$ and $R^{C5}$ are both morpholino, then B is not

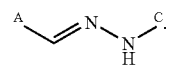

Therefore when X and Y are N, and $R^{C5}$ and $R^{C6}$ together with the carbon atoms to which they are attached form a fused $C_6$ aromatic ring, then C is either:

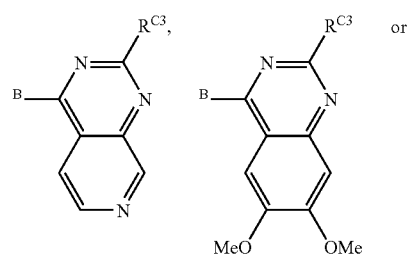

-continued

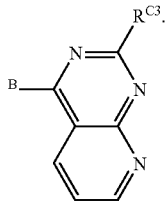

A second aspect of the present invention provides a pharmaceutical composition comprising a compound of a compound of formula I:

A-B-C  (I)

and isomers, salts, solvates, chemically protected forms, and prodrugs thereof wherein:
B is selected from the group consisting of:

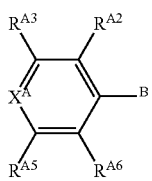

where $R^N$ is H or Me;
or B is a divalent $C_5$ heterocyclic residue containing one or two ring heteroatoms;
A is:

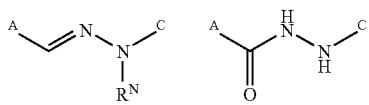

$R^{A3}$ and $R^{A5}$ are independently selected from halo, $OR^O$ and $R^{AC}$, where $R^O$ is H or Me, and $R^{AC}$ is H or $C_{1-4}$ alkyl;
$X^A$ is selected from N and $CR^{A4}$, where $R^{A4}$ is selected from H, $OR^O$, $CH_2OH$, $CO_2H$, $NHSO_2Me$ and $NHCOMe$;
$R^{A2}$ and $R^{A6}$ are independently selected from H, halo and $OR^O$;
or $R^{A3}$ and $R^{A4}$ together with the carbon atoms to which they are attached, or RA2 and $R^{A3}$ together with the carbon atoms to which they are attached, may form a $C_{5-6}$ heterocylic or heteroaromatic ring, containing at least one nitrogen ring atom;
where if X is not N, 1, 2, or 3 of $R^{A2}$ to $R^{A6}$ are not H;
C is:

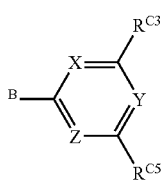

where X is selected from N and CH, Y is selected from N and CH, and Z is selected from N and $CR^{C6}$;

$R^{C3}$ is selected from H, halo and an optionally substituted N-containing $C_{5-7}$ heterocyclic group;
$R^{C5}$ is a group selected from:

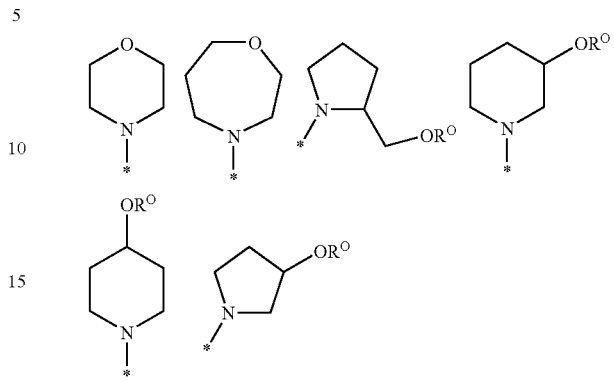

which group may be selected by one or two $C_{1-4}$ alkyl groups or a carboxy group;
$R^{C6}$ is H;
or, when X and Y are N, $R^{C5}$ and $R^{C6}$ (when Z is $CR^{C6}$) together with the carbon atoms to which they are attached may form a fused $C_6$ aromatic ring selected from the group consisting of:

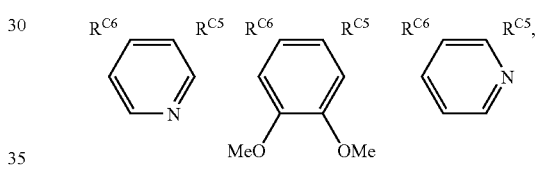

and a pharmaceutically acceptable carrier or diluent.
A third aspect of the present invention provides a compound of the second aspect for use in a method of treatment of the human or animal body.
A fourth aspect of the present invention provides the use of a compound as defined in the second aspect of the invention in the preparation of a medicament for treating a disease ameliorated by the inhibition of mTOR.
Further aspects of the invention provide the use of a compound as defined in the second aspect of the invention in the preparation of a medicament for the treatment of: cancer, immuno-suppression, immune tolerance, autoimmune disease, inflammation, bone loss, bowel disorders, hepatic fibrosis, hepatic necrosis, rheumatoid arthritis, restinosis, cardiac allograft vasculopathy, psoriasis, beta-thalassaemia, and ocular conditions such as dry eye. mTOR inhibitors may also be effective as antifungal agents
Another further aspect of the invention provides for the use of a compound as defined in the second aspect of the invention in the preparation of a medicament for use as an adjunct in cancer therapy or for potentiating tumour cells for treatment with ionizing radiation or chemotherapeutic agents.
Other further aspects of the invention provide for the treatment of disease ameliorated by the inhibition of mTOR, comprising administering to a subject in need of treatment a therapeutically-effective amount of a compound as defined in the second aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with ionizing radiation or chemotherapeutic agents.

Definitions

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl (C6).

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

N₁S₁: thiazoline (C₅), thiazolidine (C₅), thiomorpholine (C₆);
N₂O₁: oxadiazine (C₆);
O₁S₁: oxathiole (C₅) and oxathiane (thioxane) (C₆); and,
N₁O₁S₁: oxathiazine (C₆).

Examples of substituted (non-aromatic) monocyclic heterocyclyl groups include those derived from saccharides, in cyclic form, for example, furanoses (C₅), such as arabinofuranose, lyxofuranose, ribofuranose, and xylofuranse, and pyranoses (C₆), such as allopyranose, altropyranose, glucopyranose, mannopyranose, gulopyranose, idopyranose, galactopyranose, and talopyranose.

N-containing C₅₋₇ heterocyclic group: The term "N-containing C₅₋₇ heterocyclic group" as used herein refers to a 5 to 7 membered heterocylic ring containing at least one nitrogen ring atom. Examples of these groups include, but are not limited to:

N₁: pyrrolidine (tetrahydropyrrole) (C₅), pyrroline (e.g., 3-pyrroline, 2,5-dihydropyrrole) (C₅), 2H-pyrrole or 3H-pyrrole (isopyrrole, isoazole) (C₅), piperidine (C₆), dihydropyridine (C₆), tetrahydropyridine (C₆), azepine (C₇);
N₂: imidazolidine (C₅), pyrazolidine (diazolidine) (C₅), imidazoline (C₅), pyrazoline (dihydropyrazole) (C₅), piperazine (C₆);
N₁O₁: tetrahydrooxazole (C₅), dihydrooxazole (C₅), tetrahydroisoxazole (C₅), dihydroisoxazole (C₅), morpholine (C₆), tetrahydrooxazine (C₆), dihydrooxazine (C₆), oxazine (C₆);
N₁S₁: thiazoline (C₅), thiazolidine (C₅), thiomorpholine (C₆);
N₂O₁: oxadiazine (C₆);
N₁O₁S₁: oxathiazine (C₆).

Divalent C₅ heterocyclic residue: The term "divalent C₅ heterocyclic residue" as used herein, refers to a divalent moiety obtained by removing two hydrogen atoms from ring atoms of a heterocyclic compound, which moiety has 5 ring atoms. These residues have one or two ring heteroatoms. They can be derived from the groups list above as C5 heterocyclic groups.

Spiro-C₃₋₇ cycloalkyl or heterocyclyl: The term "spiro C₃₋₇ cycloalkyl or heterocyclyl" as used herein, refers to a C₃₋₇ cycloalkyl or C₃₋₇ heterocyclyl ring joined to another ring by a single atom common to both rings.

C₅₋₂₀ aryl: The term "C₅₋₂₀ aryl" as used herein, pertains to a monovalent moiety obtained by removing a hydrogen atom from an aromatic ring atom of a C₅₋₂₀ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "C₅₋₂₀ carboaryl" group.

Examples of C₅₋₂₀ aryl groups which do not have ring heteroatoms (i.e. C₅₋₂₀ carboaryl groups) include, but are not limited to, those derived from benzene (i.e. phenyl) (C₆), naphthalene (C₁₀), anthracene (C₁₄), phenanthrene (C₁₄), and pyrene (C₁₆).

Alternatively, the ring atoms may include one or more heteroatoms, including but not limited to oxygen, nitrogen, and sulfur, as in "heteroaryl groups". In this case, the group may conveniently be referred to as a "C₅₋₂₀ heteroaryl" group, wherein "C₅₋₂₀" denotes ring atoms, whether carbon atoms or heteroatoms. Preferably, each ring has from 5 to 7 ring atoms, of which from 0 to 4 are ring heteroatoms.

Examples of C₅₋₂₀ heteroaryl groups include, but are not limited to, C₅ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and C₆ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of C₅₋₂₀ heteroaryl groups which comprise fused rings, include, but are not limited to, C₉ heteroaryl groups derived from benzofuran, isobenzofuran, benzothiophene, indole, isoindole; C₁₀ heteroaryl groups derived from quinoline, isoquinoline, benzodiazine, pyridopyridine; C₁₄ heteroaryl groups derived from acridine and xanthene.

C₅₋₆ heterocyclic or heteroaromatic ring: The term "C₅₋₆ heterocyclic or heteroaromatic ring" as used herein refers to a ring which has either 5 or 6 ring atoms, and which may be fully saturated, partially unsaturated or aromatic. The ring may be one of those listed above from which C₅₋₆ heterocyclic and heteroaryl groups are derived from.

The above alkyl, heterocyclyl, and aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a C₁₋₇ alkyl group (also referred to as a C₁₋₇ alkoxy group), a C₃₋₂₀ heterocyclyl group (also referred to as a C₃₋₂₀ heterocyclyloxy group), or a C₅₋₂₀ aryl group (also referred to as a C₅₋₂₀ aryloxy group), preferably a C₁₋₇ alkyl group.

Nitro: —NO₂.

Cyano (nitrile, carbonitrile): —CN.

Acyl (keto): —C(=O)R, wherein R is an acyl substituent, for example, H, a C₁₋₇ alkyl group (also referred to as C₁₋₇ alkylacyl or C₁₋₇ alkanoyl), a C₃₋₂₀ heterocyclyl group (also referred to as C₃₋₂₀ heterocyclylacyl), or a C₅₋₂₀ aryl group (also referred to as C₅₋₂₀ arylacyl), preferably a C₁₋₇ alkyl group. Examples of acyl groups include, but are not limited to, —C(=O)CH₃ (acetyl), —C(=O)CH₂CH₃ (propionyl), —C(=O)C(CH₃)₃ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a C₁₋₇ alkyl group, a C₃₋₂₀ heterocyclyl group, or a C₅₋₂₀ aryl group, preferably a C₁₋₇ alkyl group. Examples of ester groups include, but are not limited to, —C(=O)OCH₃, —C(=O)OCH₂CH₃, —C(=O)OC(CH₃)₃, and —C(=O)OPh.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R¹ and R², together with the nitrogen atom to which they are attached, form a heterocyclic structure as in, for example, piperidinocarbonyl, morpholinocarbonyl, thiomorpholinocarbonyl, and piperazinylcarbonyl.

Amino: —NR¹R², wherein R¹ and R² are independently amino substituents, for example, hydrogen, a C₁₋₇ alkyl group (also referred to as C₁₋₇ alkylamino or di-C₁₋₇ alkylamino), a C₃₋₂₀ heterocyclyl group, or a C₅₋₂₀ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —$NHCH_3$, —$NHCH(CH_3)_2$, —$N(CH_3)_2$, —$N(CH_2CH_3)_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The cylic amino groups may be substituted on their ring by any of the substituents defined here, for example carboxy, carboxylate and amido.

Acylamido (acylamino): —$NR^1C(=O)R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —$NHC(=O)CH_3$, —$NHC(=O)CH_2CH_3$, and —$NHC(=O)Ph$. $R^1$ and $R^2$ may together form a cyclic structure, as in, for example, succinimidyl, maleimidyl, and phthalimidyl:

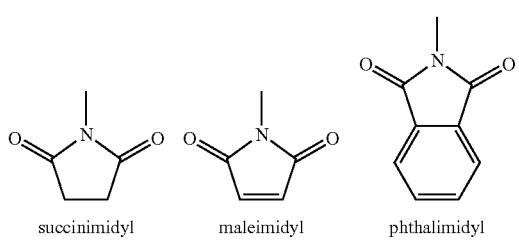

succinimidyl    maleimidyl    phthalimidyl

Ureido: —$N(R^1)CONR^2R^3$ wherein $R^2$ and $R^3$ are independently amino substituents, as defined for amino groups, and R1 is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —$NHCONH_2$, —NHCONHMe, —NHCONHEt, —$NHCONMe_2$, —$NHCONEt_2$, —$NMeCONH_2$, —NMeCONHMe, —NMeCONHEt, —$NMeCONMe_2$, —$NMeCONEt_2$ and —$NHC(=O)NHPh$.

Acyloxy (reverse ester): —$OC(=O)R$, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —$OC(=O)CH_3$ (acetoxy), —$OC(=O)CH_2CH_3$, —$OC(=O)C(CH_3)_3$, —$OC(=O)Ph$, —$OC(=O)C_6H_4F$, and —$OC(=O)CH_2Ph$.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Sulfoxide (sulfinyl): —$S(=O)R$, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —$S(=O)CH_3$ and —$S(=O)CH_2CH_3$.

Sulfonyl (sulfone): —$S(=O)_2R$, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —$S(=O)_2CH_3$ (methanesulfonyl, mesyl), —$S(=O)_2CF_3$, —$S(=O)_2CH_2CH_3$, and 4-methylphenylsulfonyl (tosyl).

Thioamido (thiocarbamyl): —$C(=S)NR^1R^2$, wherein $R^1$ and $R^2$ are independently amino substituents, as defined for amino groups. Examples of amido groups include, but are not limited to, —$C(=S)NH_2$, —$C(=S)NHCH_3$, —$C(=S)N(CH_3)_2$, and —$C(=S)NHCH_2CH_3$.

Sulfonamino: —$NR^1S(=O)_2R$, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —$NHS(=O)_2CH_3$, —$NHS(=O)_2Ph$ and —$N(CH_3)S(=O)_2C_6H_5$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

Further Preferences

The following preferences can apply to each aspect of the present invention, where applicable. The preferences for each group may be combined with those for any or all of the other groups, as appropriate.

The proviso that when X and Y are N and Z is N or CH, $R^{C3}$ and $R^{C5}$ are both morpholino, then B is not

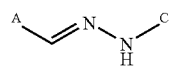

may apply to any aspect of the present invention.

A

A is preferably:

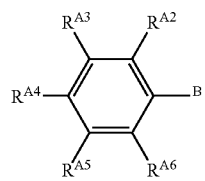

where $R^{A2}$ to $R^{A6}$ are as defined above.

Where $R^{A3}$ and $R^{A4}$ together with the carbon atoms to which they are attached, or $R^{A2}$ and $R^{A3}$ together with the carbon atoms to which they are attached, form a $C_{5-6}$ heterocylic or heteroaromatic ring, containing at least one nitrogen ring atom and the ring is aromatic then exemplary groups include, but are not limited to, pyridine, pyrrole (e.g. azole), imidazole (e.g. 1H-imidazole), triazole (e.g. 1-Me-triazole). If the ring is not aromatic, it may be oxazolone.

$R^{AC}$ may be selected from methyl and t-butyl, and in some embodiments is preferably methyl.

It may be preferred that $R^{A4}$ is only H, when $R^{A3}$ and $R^{A5}$ are OH.

$R^{A2}$ and $R^{A6}$ may preferably be selected from H and $OR^O$.

In some embodiments, A is:

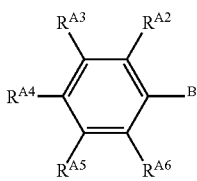

where $R^{A3}$ and $R^{A5}$ are independently selected from halo, $OR^O$ and $R^O$, where $R^O$ is H or Me;
$R^{A4}$ is selected from $OR^O$, $CO_2H$, $NHSO_2Me$ and NHCOMe; or, when $R^{A3}$ and $R^{A5}$ are OH,
$R^{A4}$ may be H;
$R^{A2}$ and $R^{A6}$ are independently selected from H and $OR^O$;
where 1, 2, or 3 of $R^{A2}$ to $R^{A6}$ are not H.

It is preferred that 2 or 3 of $R^{A2}$ to $R^{A6}$ are not H, and it is more preferred that 3 of $R^{A2}$ to $R^{A6}$ are not H. Those of $R^{A2}$ to $R^{A6}$ which are not H are preferably $OR^O$, and more preferably OH.

It is preferred that $R^{A4}$ is $OR^O$, and more particularly OH.

$R^{A3}$ and $R^{A5}$ are preferably independently selected from H and $OR^O$, and more preferably selected from H and OH.

$R^{A2}$ and $R^{A6}$ are preferably independently selected from H and OH.

Preferred A groups are: 2,3,4-trihydoxy phenyl; 3,4,5-trihydroxy phenyl; 2,4,6-trihydoxy phenyl; 3,4-dihydroxy phenyl; and 3,5-dimethoxy, 4-hydroxy phenyl.

B

If B is a divalent $C_5$ heterocyclic residue, it is preferred that the ring atoms bound to A and C are separated by a further ring atom. It may be preferred that at least one ring atom is nitrogen, in which case, it is further preferred that there are two ring heteroatoms, the second being selected from nitrogen and sulphur. If there is only a single ring heteroatom, this is preferably selected from oxygen and sulphur.

B may be selected from the group consisting of:

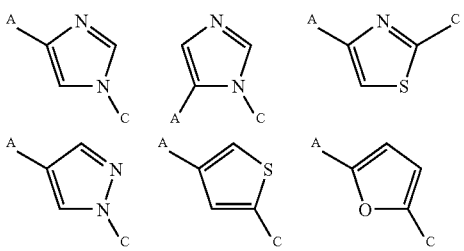

In some embodiments, B may be selected from the group consisting of:

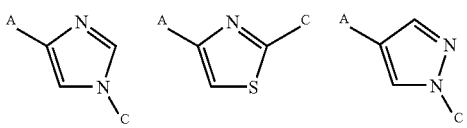

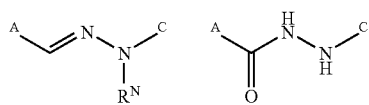

In some aspects of the invention, it is preferred that B is not:

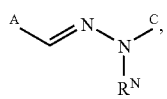

where $R^N$ is H.
It may be preferred that B is not

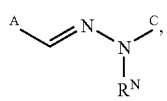

where $R^N$ is as defined for formula I.
B is preferably selected from the group consisting of:

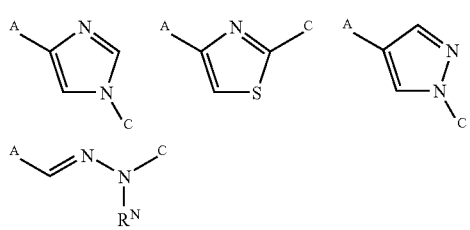

where $R^N$ is H or Me, and is preferably H.
B is preferably selected from:

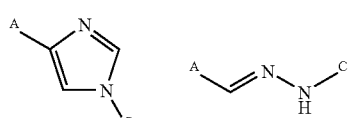

C

If X and Y are N, and $R^{C5}$ and $R^{C6}$ together with the carbon atoms to which they are attached form a fused $C_6$ aromatic ring, then C may be selected from:

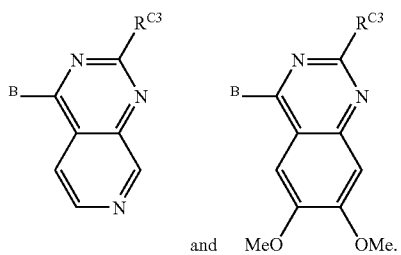

If X and Y are N, and $R^{C5}$ and $R^{C6}$ together with the carbon atoms to which they are attached form a fused $C_6$ aromatic ring, then $R^{C3}$ is preferably H, and C is more preferably:

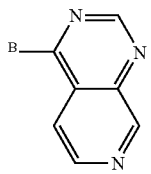

It is preferred that at least two of X, Y and Z are N, and more preferred that all of X, Y and Z are N.

If two of X, Y and Z are N, then it is preferred that Z and one of X and Y is N. It is more preferred for Z and Y to be N.

When less than 3 of X, Y and Z are N, it is preferred that $R^{C3}$ is selected from H and an optionally substituted N-containing $C_{5-6}$ heterocyclic group.

Preferred optionally substituted N-containing $C_{5-7}$ heterocyclic groups for $R^{C3}$ include, but are not limited to, morpholino, thiomorpholino, piperadinyl, piperazinyl (preferably N-substituted), homopiperazinyl (preferably N-substituted) and pyrrolidinyl.

Preferred N-substituents for the piperazinyl and homopiperazinyl groups include esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$.

More preferred N-containing $C_{5-7}$ heterocyclic groups are morpholino and piperadinyl, with morpholino being the most preferred. These groups are preferably unsubstituted.

Preferred groups for $R^{C5}$ include those where $R^O$ is H.

A particularly preferred group for $R^{C5}$ is morpholino, which in some embodiments is preferably substituted, and in other embodiments is preferably unsubstituted.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in ref. 25.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, ref. 26.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc); as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C$_{1-20}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleared by phosphotase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

General Synthesis

When B is selected from:

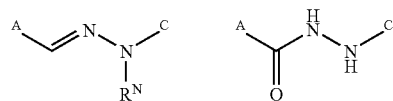

compounds of formula I may be represented as Formula 1a:

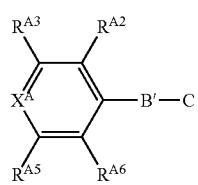

Formula 1a where B' represents the two possible B groups.

Where B' is:

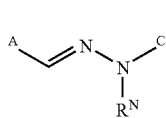

compounds of Formula 1a may be synthesised by coupling a compound of Formula 2:

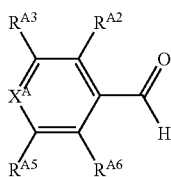

Formula 2 with a compound of Formula 3:

Formula 3 in the presence of a catalytic amount of p-toluenesulfonic acid, or a similar compound.

Where B' is:

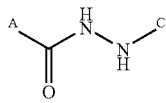

compounds of Formula 1a may be synthesised by coupling a compound of Formula 4:

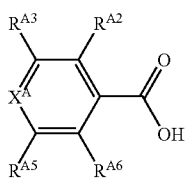

Formula 4 with a compound of Formula 3:

Formula 3 in the presence of an amide coupling agent, such as O-(7-Azabenzotriazol-1-yl)-N,N,N',N'-tetramethyluronium hexafluorophosphate.

Compounds of Formula 3 may be synthesised may be synthesised from a compound of Formula 5:

Formula 5 by the addition of hydrazine hydrate or methyl hydrazine in an organic solvent. Microwave heating may be used as an alternative to conventional heating.

Compounds of Formula 5 where C is:

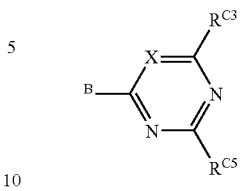

where X is N or CH, can be represented by Formula 5a:

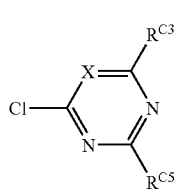

Formula 5a

Compounds of Formula 5a where $R^{C3}$ is an optionally substituted N-containing $C_{5-7}$ heterocyclic group can be synthesised from a compound of Formula 5a where $R^{C3}$ is halo, e.g. Cl, by reacting them with an appropriate amine. Such compounds can be synthesised from a compound where $R^{C5}$ is halo, e.g. Cl, in a similar manner. If $R^{C3}$ and $R^{C5}$ are the formed from the same amine, these steps are preferably carried out simultaneously.

The synthesis of compounds of Formula 5, where C is:

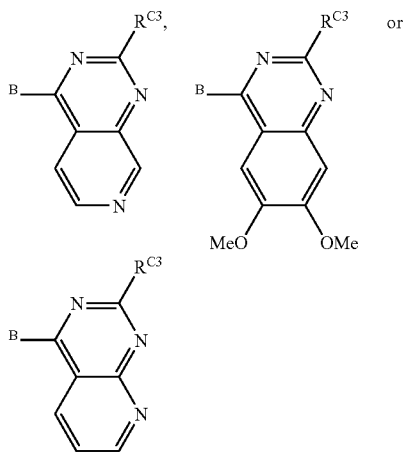

are illustrated in Examples 4, 5 and 15 below, which methods can be adapted to introduce an $R^{C3}$ group as appropriate.

When C is:

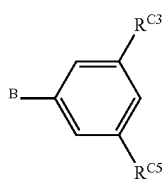

and B is:

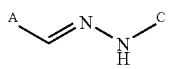

compounds of Formula 3:

 Formula 3 may be represented as Formula 3a:

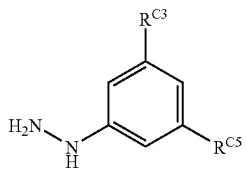 Formula 3a which may be synthesised from a compound of Formula 6:

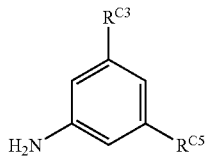 Formula 6 by reaction with sodium nitrite and tin (II) chloride dihydrate Compounds of Formula 6 can be readily synthesised using known methods.

When B is a divalent $C_5$ heterocyclic residue containing one or two ring heteroatoms compounds of formula I may be represented as Formula 1b:

A-B"—C    Formula 1b where B" represents the possible B groups.

Compounds of Formula 1b where A is:

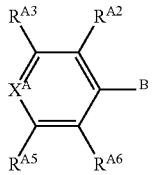

may be synthesised from compounds of Formula 1b where A is Br—, by coupling an appropriate boronic acid or ester, using Suzuki conditions.

Compounds of Formula 1b where A is Br—, may be synthesised from compounds of Formula 5:

 Formula 5 by addition of a compound of Formula 7:

 Formula 7 with sodium hydride in an appropriate organic solvent.

Alternatively a precursor of a compound of Formula 5 may be coupled to a compound of Formula 7, and then the final transformation of group C carried out, before continuing the synthesis.

Use

The present invention provides active compounds, specifically, active in inhibiting the activity of mTOR.

The term "active" as used herein, pertains to compounds which are capable of inhibiting mTOR activity, and specifically includes both compounds with intrinsic activity (drugs) as well as prodrugs of such compounds, which prodrugs may themselves exhibit little or no intrinsic activity.

One assay which may conveniently be used in order to assess the mTOR inhibition offered by a particular compound is described in the examples below.

The present invention further provides a method of inhibiting the activity of mTOR in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect", the inhibition of cellular growth in a certain time or the accumulation of cells in the G1 phase of the cell cycle over a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimes of drugs and/or ionising radiation as used in the treatment of different cancer types. Examples of adjunct anti-cancer agents that could be combined with compounds from the invention include, but are not limited to, the following: alkylating agents: nitrogen mustards, mechlorethamine, cyclophosphamide, ifosfamide, melphalan, chlorambucil: Nitrosoureas: carmustine (BCNU), lomustine (CCNU), semustine (methyl-CCNU), ethylenimine/methylmelamine, thriethylenemelamine (TEM), triethylene thiophosphoramide (thiotepa), hexamethylmelamine (HMM, altretamine): Alkyl sufonates; busulfan; Triazines, dacarbazine (DTIC): Antimetabolites; folic acid analogs, methotrexate, trimetrexate, pyrimidine analogs, 5-fluorouracil, fluorodeoxyuridine, gemcitabine, cytosine arabinoside (AraC, cytarabine), 5-azacytidine, 2,2'-difluorodeoxycytidine: Purine analogs; 6-mercaptopurine, 6-thioguanine, azathioprine, 2'-deoxycoformycin (pentostatin, erythrohydroxynonyladenine (EHNA), fludarabine phosphate, 2-Chlorodeoxyadenosine (cladribine, 2-CdA): Topoisomerase I inhibitors; camptothecin, topotecan, irinotecan, rubitecan: Natural products; antimitotic drugs, paclitaxel, vinca alkaloids, vinblastine (VLB), vincristine, vinorelbine, Taxotere™ (docetaxel), estramustine, estramustine phosphate; epipodophylotoxins, etoposide, teniposide: Antibiotics; actimomycin D, daunomycin (rubidomycin), doxorubicin (adriamycin), mitoxantrone, idarubicin, bleomycins, plicamycin (mithramycin), mitomycin C, dactinomycin: Enzymes; L-asparaginase, RNAse A: Biological response modifiers; interferon-alpha, IL-2, G-CSF, GM-CSF: Differentiation Agents; retinoic acid derivatives: Radiosensitizers;. metronidazole, misonidazole, desmethylmisonidazole, pimonidazole, etanidazole, nimorazole, RSU 1069, EO9, RB 6145, SR4233, nicotinamide, 5-bromodeozyuridine, 5-iododeoxyuridine, bromodeoxycytidine: Platinum coordination complexes; cisplatin, carboplatin: Anthracenedione; mitoxantrone, AQ4N Substituted urea, hydroxyurea; Methylhydrazine derivatives, N-methylhydrazine (MIH), procarbazine; Adrenocortical suppressant, mitotane (o.p'-DDD), aminoglutethimide: Cytokines; interferon ($\alpha$, $\beta$, $\gamma$), interleukin; Hormones and antagonists; adrenocorticosteroids/antagonists, prednisone and equivalents, dexamethasone, aminoglutethimide; Progestins, hydroxyprogesterone caproate, medroxyprogesterone acetate, megestrol acetate; Estrogens, diethylstilbestrol, ethynyl estradiol/equivalents; Antiestrogen, tamoxifen; Androgens, testosterone propionate, fluoxymesterone/equivalents; Antiandrogens, flutamide, gonadotropin-releasing hormone analogs, leuprolide; Nonsteroidal antiandrogens, flutamide; EGFR inhibitors, VEGF inhibitors; Proteasome inhibitors.

Active compounds may also be used as cell culture additives to inhibit mTOR, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

Cancer

The present invention provides active compounds which are anticancer agents or adjuncts for treating cancer. One of ordinary skill in the art is readily able to determine whether or not a candidate compound treats a cancerous condition for any particular cell type, either alone or in combination.

Examples of cancers include, but are not limited to, lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma and leukemias.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, refs. 27 to 29.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoro-ethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

General Experimental Methods

Thin Layer chromatography was carried out using Merck Kieselgel 60 $F_{254}$ glass backed plates. The plates were visualized by the use of a UV lamp (254 nm). Silica gel 60 (particle sizes 40-63 µm) supplied by E.M. Merck was employed for flash chromatography. $^1$H NMR spectra were recorded at 300 MHz on a Bruker DPX-300 instrument. Chemical shifts were referenced relative to tetramethylsilane.

Purification and Identification of Library Samples

The samples were purified on Gilson LC units. Mobile phase A—0.1% aqueous TFA, mobile phase B—Acetonitrile; flow rate 6 ml/min; Gradient—typically starting at 90% A/10% B for 1 minute, rising to 97% after 15 minutes, holding for 2 minutes, then back to the starting conditions. Column: Jones Chromatography Genesis 4 µm, C18 column, 10 mm×250 mm. Peak acquisition based on UV detection at 254 nm.

Mass spectra were recorded on a Finnegan LCQ instrument in positive ion mode. Mobile phase A—0.1% aqueous formic acid. Mobile phase B—Acetonitrile; Flowrate 2 ml/min; Gradient—starting at 95% A/5% B for 1 minute, rising to 98% B after 5 minutes and holding for 3 minutes before returning to the starting conditions. Column: Varies, but always C18 50 mm×4.6 mm (currently Genesis C18 4 µm. Jones Chromatography). PDA detection Waters 996, scan range 210-400 nm.

Microwave Synthesis

Reactions were carried out using a Personal Chemistry™ Emrys Optimiser microwave synthesis unit with robotic arm. Power range between. 0-300 W at 2.45 GHz. Pressure range between 0-20 bar; temperature increase between 2-5° C./sec; temp range 60-250° C.

Example 1a

Synthesis of 6-(N'-Methylene-hydrazino)-[1,3,5]triazine-2,4-diamine derivatives (5)

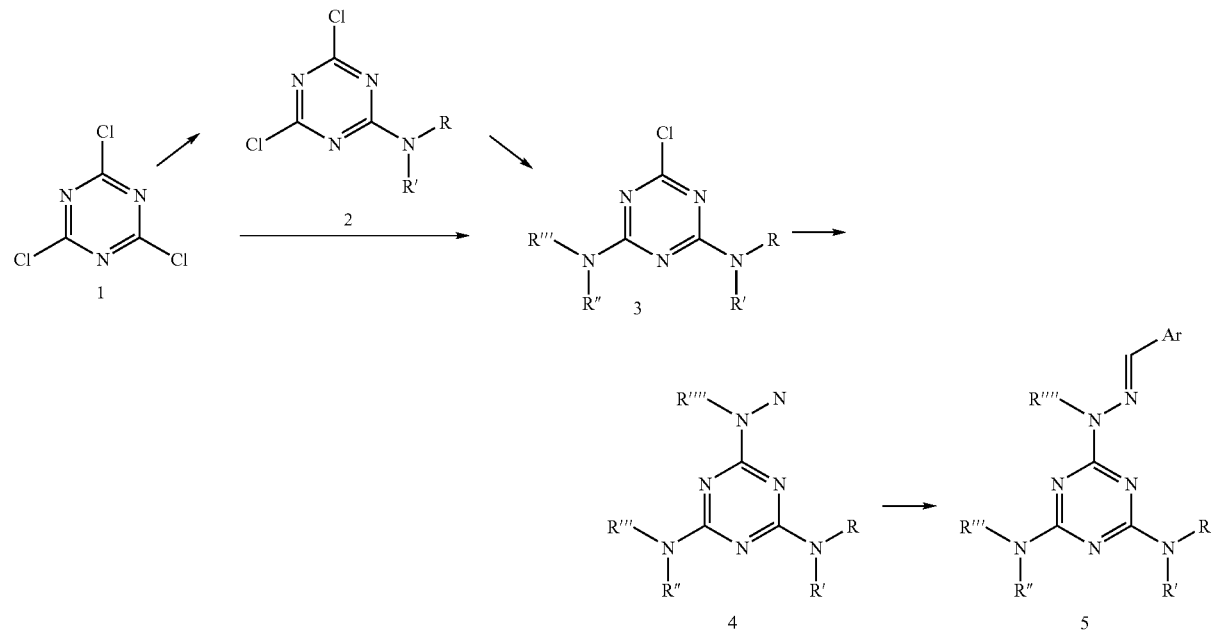

(i) Synthesis of 4,6-Dichloro-[1,3,5]triazin-2-ylamine Derivatives (2)

To a cooled (−60° C.) solution of cyanuric chloride (1) (3.00 g, 16.26 mmol) in ethyleneglycol dimethylether (40 ml) was added a solution of the appropriate amine (2.80 ml, 32.5 mmol) in water (1.4 ml). The amine solution was added in a dropwise manner over the period of 10 minutes. The mixture was removed from the cooling bath and water added which fully quenched (25 ml) the reaction. The quenched mixture was stirred for 5 minutes before being filtered to remove any precipitate. The filter cake was washed with water (250 ml) and dried in a vacuum desiccator to give the desired 4,6-dichloro-[1,3,5]triazin-2-ylamine which was then purified further by recrystallisation from the minimum amount of hot EtOAc to give the product.

| Compound | NRR' | Yield % | m/z [M + H]⁺ | RT (mins) |
|---|---|---|---|---|
| 2a | 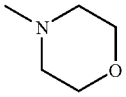 morpholine | 35 | 236 | 0.64 |

| Compound | NRR' | NR"R'" | Yield % | m/z [M + H]⁺ | RT (mins) |
|---|---|---|---|---|---|
| 3a | *–N(morpholine) | *–N(piperidine) | 52 | 284 | 4.90 |
| 3b | *–N(morpholine) | *–N(morpholine) | 78 | 286 | 5.69 |

(iia) Synthesis of 6-Chloro-[1,3,5]triazine-2,4-diamine Derivatives (3) (where amine groups different)

To a cooled (−50° C.) solution of appropriate 4,6-dichloro-[1,3,5]triazin-2-yl amine (2)(0.35 mmol) in dimethylformamide (5 ml) was added powdered $K_2CO_3$ (1.14 mmol) and then the appropriate amine (0.35 mmol) was added in a dropwise manner. The mixture was stirred at −50° C. for 10 mins and then allowed to warm slowly to room temperature. Ethyl acetate (10 ml) and water (10 ml) was added to the reaction mixture. The organic extract was removed, washed with saturated brine solution, dried ($MgSO_4$), filtered and concentrated in vacuo to typically give a crystalline solid as the desired product in a suitably pure form to be used without any further purification.

(iib) Synthesis of 6-Chloro-[1,3,5]triazine-2,4-diamine Derivatives (3) (where amine groups same)

To a cooled (0° C.) solution of cyanuric chloride (1)(3 g, 16.3 mmol) in acetone (50 ml) was added a solution of the appropriate amine (68.7 mmol) in water (2.99 ml). The solution became turbid white as a precipitate formed immediately. The reaction was maintained at 0° C. for 80 minutes whereupon more water was added to the mixture (100 ml) and the solid removed by filtration. The filtercake was washed with cold water (50 ml) and dried in a vacuum desiccator to typically give a white solid as the desired product in a suitably pure form to be used without any further purification.

(iii) Synthesis of 6-Hydrazino-[1,3,5]triazine-2,4-diamine derivatives (4)

(a) To a suspension of the appropriate 6-chloro-[1,3,5]triazine-2,4-diamine (3)(20 mmol) in ethanol (25 ml) was added hydrazine hydrate (5 ml, 100 mmol). The mixture was then heated to reflux and maintained at this temperature for 3 hours. After this time the mixture was cooled to room temperature where the solid was filtered and washed with ethanol (2×20 ml) to give the desired product as a white crystalline solid that was suitably pure to be used without any further purification (b) A suspension of the appropriate 6-chloro-[1,3,5]triazine-2,4-diamine (3)(3.5 mmol) in methyl hydrazine (5 ml) was heated to reflux for 5 hours. The mixture was then cooled to 0° C. and water (10 ml) added. The resulting precipitate was then removed from the mixture by filtration and washed with water (2×10 ml) to give the title compound as a colourless solid that was suitably clean to be used without any further purification.

| Compound | NRR' | NR"R'" | R"" | Yield % | m/z [M + H]⁺ | RT (mins) |
|---|---|---|---|---|---|---|
| 4a | *–N(morpholine) | *–N(morpholine) | H | 98 | 282 | 2.91 |

-continued

| Compound | NRR' | NR"R'" | R"" | Yield % | m/z [M + H]+ | RT (mins) |
|---|---|---|---|---|---|---|
| 4b | *-N(morpholine) | *-N(morpholine) | Me | 99 | 296 | 3.04 |
| 4c | *-N(morpholine) | *-N(piperidine) | H | 66 | 280 | 3.28 |
| 4d | *-N(morpholine) | *-N(piperidine) | Me | 50 | 294 | 3.29 |

(iv) Synthesis of 6-(N'-Methylene-hydrazino)-[1,3,5]triazine-2,4-diamine derivatives (5)

(a) To a mixture of the appropriate 6-hydrazino-[1,3,5]triazine-2,4-diamine derivative (4)(0.71 mmol) in ethanol (4 ml) was added the appropriate aldehyde (0.71 mmol) and catalytic p-toluenesulfonic acid (0.04 mmol, 4.3 mg). The mixture was heated under the influence of microwave radiation to 130° C. for 600 seconds (fixed hold time, pre-stirred for 20 seconds. Upon further cooling (0° C.) a precipitate formed which was removed by suction filtration. The filter cake was then washed with ice cold ethanol (5 ml) to give the desired product.

(b) To a solution of the appropriate 6-hydrazino-[1,3,5]triazine-2,4-diamine derivative (4)(0.50 mmol) in ethanol (2 ml) was added the appropriate aldehyde (0.50 mmol) and catalytic p-toluenesulfonic acid (0.036 mmol, 6.1 mg). The mixture was then cooled (0° C.) which caused a precipitate to form. The solid was removed by suction filtration and washed with ice cold ethanol (5 ml) to give the desired product.

| | NRR' | NR"R'" | R"" | Ar | Purity % | m/z [M + H]+ | RT (mins) |
|---|---|---|---|---|---|---|---|
| 5a | *-N(morpholine) | *-N(morpholine) | H | 3,4,5-trihydroxyphenyl | 99 | 418 | 3.28 |
| 5b | *-N(morpholine) | *-N(morpholine) | H | 2,3,4-trihydroxyphenyl | 90 | 418 | 3.64 |
| 5c | *-N(morpholine) | *-N(morpholine) | H | 3,5-dibromo-4-hydroxyphenyl | 99 | 544 | 4.51 |
| 5d | *-N(morpholine) | *-N(morpholine) | H | 4-hydroxy-3-methoxyphenyl | 100 | 416 | 3.46 |

-continued

| | NRR' | NR"R''' | R'''' | Ar | Purity % | m/z [M + H]+ | RT (mins) |
|---|---|---|---|---|---|---|---|
| 5e | *-morpholine | *-morpholine | H | 2,4,6-trihydroxyphenyl* | 88 | 418 | 3.65 |
| 5f | *-morpholine | *-morpholine | H | 3,5-dihydroxyphenyl* | 94 | 402 | 3.38 |
| 5g | *-morpholine | *-morpholine | H | 4-hydroxy-3,5-dimethylphenyl* | 99 | 414 | 3.65 |
| 5h | *-morpholine | *-morpholine | H | 4-hydroxyphenyl* | 100 | 386 | 3.36 |
| 5i | *-morpholine | *-morpholine | H | 4-(methylsulfonylamino)phenyl* | 97 | 463 | 3.54 |
| 5j | *-morpholine | *-morpholine | H | 4-methoxyphenyl* | 100 | 400 | 3.72 |
| 5k | *-morpholine | *-morpholine | H | 4-acetamidophenyl* | 97 | 427 | 3.36 |
| 5l | *-morpholine | *-morpholine | Me | 2,3,4-trihydroxyphenyl* | 100 | 432 | 4.08 |
| 5m | *-morpholine | *-morpholine | Me | 3,4,5-trihydroxyphenyl* | 98 | 432 | 3.28 |

-continued

| | NRR' | NR"R''' | R"" | Ar | Purity % | m/z [M + H]+ | RT (mins) |
|---|---|---|---|---|---|---|---|
| 5n | *-morpholine | *-morpholine | Me | 3,4-dihydroxyphenyl | 100 | 416 | 3.4 |
| 5o | *-morpholine | *-morpholine | Me | 2,4,6-trihydroxyphenyl | 96 | 432 | 3.98 |
| 5p | *-morpholine | *-morpholine | Me | 3,5-dihydroxyphenyl | 100 | 416 | 3.4 |
| 5q | *-morpholine | *-morpholine | Me | 3,5-dimethoxy-4-hydroxyphenyl | 97 | 460 | 3.5 |
| 5r | *-morpholine | *-piperidine | H | 3,5-dimethoxy-4-hydroxyphenyl | 98 | 444 | 3.68 |
| 5s | *-morpholine | *-morpholine | H | 3,5-di-tert-butyl-4-hydroxyphenyl | 99 | 498 | 4.60 |
| 5t | *-morpholine | *-morpholine | Me | 2,5-dihydroxyphenyl | 100 | 432 | 3.89 |
| 5u | *-morpholine | *-morpholine | H | 1-methyl-1H-benzotriazol-5-yl | 95 | 245.5 | 3.40 |

| | NRR' | NR"R"' | R"" | Ar | Purity % | m/z [M + H]+ | RT (mins) |
|---|---|---|---|---|---|---|---|
| 5v | *−N(morpholine) | *−N(morpholine) | H | benzimidazole | 85 | 410.4 | 2.38 |
| 5w | *−N(morpholine) | *−N(morpholine) | H | benzoxazolone | 90 | 427.0 | 2.75 |
| 5x | *−N(morpholine) | *−N(morpholine) | H | 4-carboxyphenyl | 100 | 414 | 3.52 |

Example 1(b)

Synthesis of 4-[(4-Chloro-6-morpholin-4-yl-[1,3,5]triazin-2-yl)-hydrazonomethyl]-2,6-dimethoxy-phenol (7)

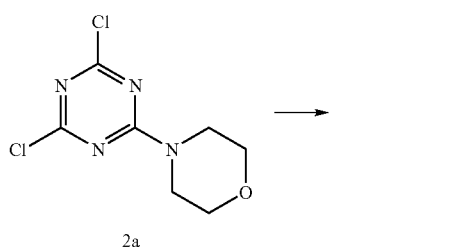

2a

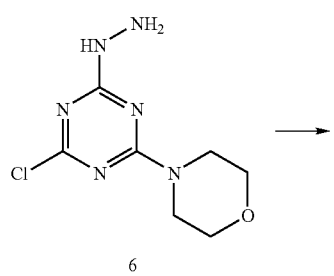

6

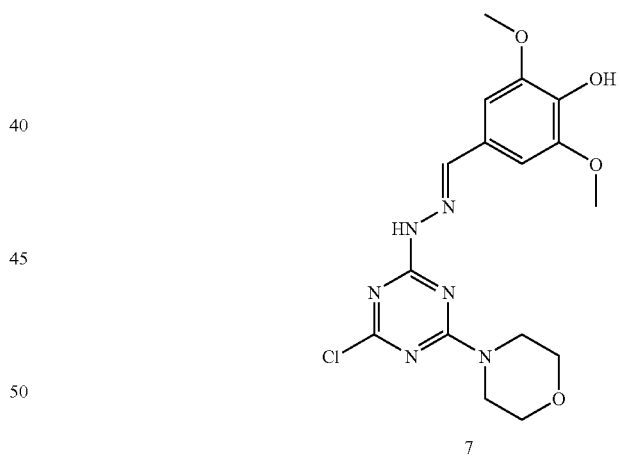

7

(i) (4-Chloro-6-morpholin-4-yl-[1,3,5]triazin-2-yl)-hydrazine (6)

This was synthesized from (2a) using the method of Example 1a(iii) to give a yield of 99%. M/Z (LC-MS, ESP): 231 [M+H]+, R/T=2.93 mins.

(ii) 4-[(4-Chloro-6-morpholin-4-yl-[1,3,5]triazin-2-yl)-hydrazonomethyl]-2,6-dimethoxy-phenol (7)

This was synthesized from (6) using the method of Example 1a(iv). M/Z (LC-MS, ESP): Purity 97%, 395 [M+H]+, R/T=4.08 mins.

Example 2

Synthesis of 6-(N'-Methylene-hydrazino)-pyrimidine-2,4-diamine derivatives (12)

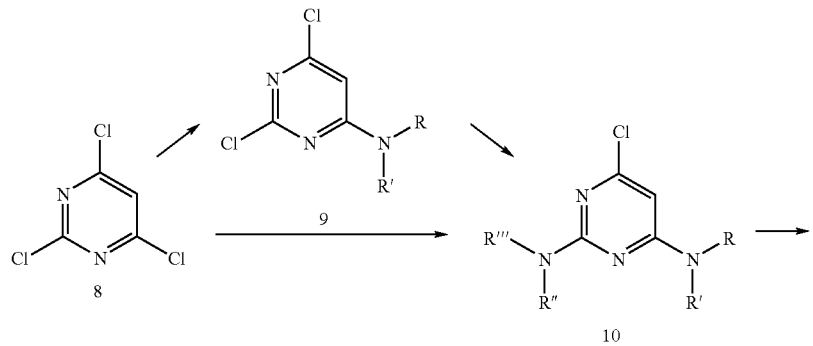

(i) Synthesis of 2,6-Dichloro-pyrimidin-4-ylamine Derivatives (9)

To a cooled (−5° C.) solution of 2,4,6-trichloro-pyrimidine (8)(2.73 mmol) in ethanol (6 ml) was added the appropriate amine (2.73 mmol) and then $Et_3N$ (0.303 ml, 2.18 mmol) which was added in a dropwise fashion. The cooling bath was removed and the reaction allowed to warm to room temperature. Water was then added to the mixture which caused a precipitate to form. The solid was removed by suction filtration and washed with ice cold EtOH (6 ml) to give the desired product which was then purified by flash chromatography (eluent typically 100% Hexanes going to 4:1—Hexanes: EtOAc)

| Compound | NRR' | Yield % | m/z [M + H]$^+$ | RT (mins) |
|---|---|---|---|---|
| 9a | *–N(morpholine) | 85 | 235 | 4.02 |

(iia) Synthesis of 6-Chloro-pyrimidine-2,4-diamine Derivatives (10) (where amine groups different)

To a solution of the appropriate 2,6-dichloro-pyrimidin-4-ylamine derivative (9)(0.85 mmol) in THF/EtOH (2:1, 1.5 ml) was added the appropriate amine (2.13 mmol) in ethanol (1 ml). The mixture was stirred at room temperature overnight and cooled to 0° C. whereupon a precipitate formed. The solid was removed by suction filtration, washed with ice cold ethanol and dried in a vacuum desiccator to give the desired product.

| | NRR' | NR"R'" | Yield % | m/z [M + H]+ | RT (mins) |
|---|---|---|---|---|---|
| 10a | *–N(morpholine) | *–N(piperidine) | 85 | 283 | 5.09 |
| 10b | *–N(morpholine) | *–N(pyrrolidine) | 74 | 269 | 4.50 |
| 10c | *–N(morpholine) | *–N(piperazine-N-Boc) | 100 | 385 | 5.01 |
| 10d | *–N(morpholine) | *–N(homopiperazine-N-Boc) | 100 | 398 | 4.91 |

(iib) Synthesis of 6-Chloro-pyrimidine-2,4-diamine Derivatives (10) (where amine groups same)

Compound 10e was made by the method of Example 2(iia) using double the amount of morpholine.

Compound 10f was made as follows: To a cooled (0° C.) solution of 2,4,6-trichloropyrimidine (8)(1.23 g, 6.7 mmol) in THF (40 ml) under an inert atmosphere was added piperidine (3.32 ml, 33.6 mmol) which caused a white precipitate to form that made stirring difficult. The mixture was heated to 50° C. for 24 hrs whereupon it was cooled to room temperature and diluted with water (40 ml). The organic extract was removed, dried using $MgSO_4$, filtered and concentrated in vacuo to give a colourless solid. The crude residue was purified by flash chromatography ($SiO_2$) (70:30 going to 60:40—Hexanes:EtOAc as eluent) to give the desired product (1.62 g, 86%) in analytically pure form.

| | NRR' | NR"R'" | Yield % | m/z [M + H]+ | RT (mins) |
|---|---|---|---|---|---|
| 10e | *–N(morpholine) | *–N(morpholine) | 90 | 286 | 4.24 |
| 10f | *–N(piperidine) | *–N(piperidine) | 97 | 281 | 5.69 |

(iii) Synthesis of 6-hydrazino-pyrimidine-2,4-diamine Derivatives (11)

To suspension of the appropriate 6-Chloro-pyrimidine-2,4-diamine derivative (0.85 mmol) in 1-butanol (1.0 ml) was added hydrazine hydrate (1.0 ml) The mixture was heated to reflux and maintained at this temperature with stirring for 48 hours. The mixture was cooled to room temperature and concentrated in vacuo to typically give a red sticky residue. The residue was triturated with EtOH to give a colourless solid.

| | NRR' | NR"R'" | R"" | Yield % | m/z [M + H]+ | RT (mins) |
|---|---|---|---|---|---|---|
| 11a | *–N(morpholine) | *–N(morpholine) | H | 99 | 282 | 2.88 |

-continued
| | NRR' | NR"R''' | R'''' | Yield % | m/z [M + H]+ | RT (mins) |
|---|---|---|---|---|---|---|
| 11b | 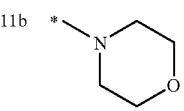 | 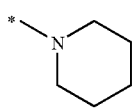 | H | 80 | 279 | 3.32 |
| 11c | 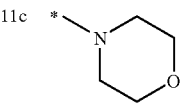 | 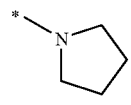 | H | 74 | 295 | 3.16 |
| 11d | 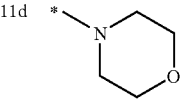 | 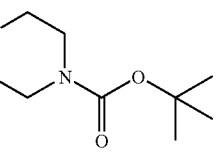 | H | 99 | 380 | 3.47 |
| 11e | 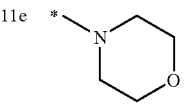 | 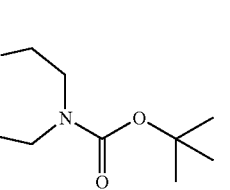 | H | 80 | 394 | 3.47 |
(iv) Synthesis of 6-(N'-Methylene-hydrazino)-pyrimidine-2,4-diamine derivatives (12)
These were synthesized from 11 using the method of Example 1a(iv).
| | NRR' | NR"R''' | R'''' | Ar | Purity % | m/z [M + H]+ | RT (mins) |
|---|---|---|---|---|---|---|---|
| 12a | 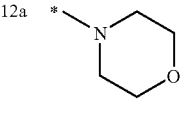 | 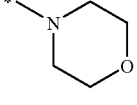 | H | 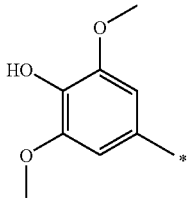 | 99 | 445 | 3.44 |
| 12b | 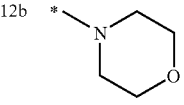 | 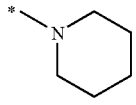 | H | 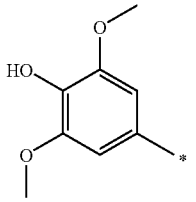 | 97 | 443 | 4.31 |
| 12c | 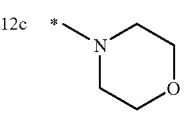 | 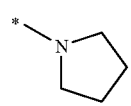 | H | 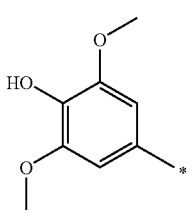 | 95 | 429 | 3.65 |

-continued

| | NRR' | NR"R''' | R"" | Ar | Purity % | m/z [M + H]+ | RT (mins) |
|---|---|---|---|---|---|---|---|
| 12d | *-morpholine | *-piperazine-N-Boc | H | 3,5-dimethoxy-4-hydroxyphenyl-* | 97 | 544 | 3.97 |
| 12e | *-morpholine | *-piperazine-N-Boc | H | 3,4-dihydroxyphenyl-* | 96 | 500 | 3.94 |
| 12f | *-morpholine | *-homopiperazine-N-Boc | H | 3,5-dimethoxy-4-hydroxyphenyl-* | 96 | 558 | 3.85 |
| 12g | *-morpholine | *-homopiperazine-N-Boc | H | 3,4-dihydroxyphenyl-* | 92 | 364 | 3.45 |
| 12h | *-morpholine | *-morpholine | H | 3,4-dihydroxyphenyl-* | 100 | 416 | 3.38 |
| 12i | *-morpholine | *-morpholine | H | 4-hydroxyphenyl-* | 98 | 400 | 3.49 |

Example 3a

Synthesis of 2,6-dimethoxy-phenol-4-boronic acid (15)

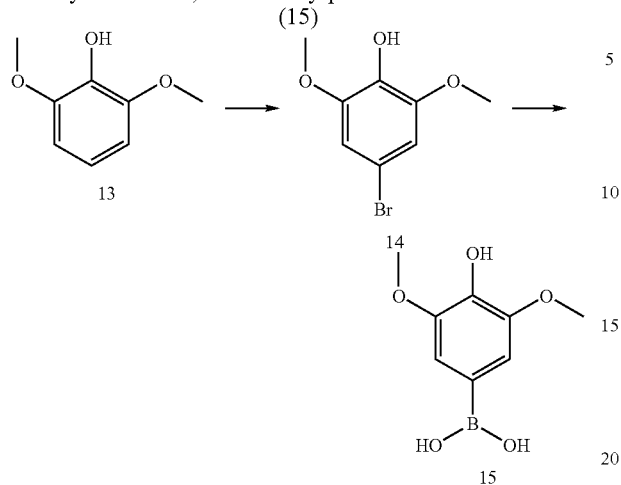

(i) 4-Bromo-2,6-dimethoxy-phenol (14)

To a cooled (−78° C.) solution of 2,6-dimetoxyphenol (13) (15 g, 97.35 mmol) in CH$_2$Cl$_2$ (200 ml) was added N-bromosuccinimide (17.4 g, 97.35 mmol) portionwise over twenty minutes. The reaction mixture was stirred at −78° C. under an inert atmosphere for four hours before being allowed to warm to room temperature where it was stirred for a further 16 hours. The solvent was then removed in vacuo to give a slurry that was purified by flash chromatography (SiO$_2$) (7:3—CH$_2$Cl$_2$:Hexanes) and then re-crystallised from CH$_3$Cl/hexanes to give the title compound as a white solid that was analytically clean (9.66 g, 42.57%). m/z (LC-MS, ESP): 231 [M−H]$^-$, R/T=3.17 mins

(ii) 2,6-dimethoxy-phenol-4-boronic acid (15)

To a solution of 4-Bromo-2,6-dimethoxy-phenol (14)(9.32 g, 40 mmol) in anhydrous diethyl ether (100 ml) was added triisopropyl borate (11 ml, 48 mmol). The reaction mixture was cooled to −78° C. and n-butyl lithium (1.7 M in pentane, 56 ml, 96 mmol) added under an inert atmosphere. The solution was stirred at −78° C. for a further 5 hours and then allowed to warm to room temperature and maintained like this, with stirring, for a further 16 hours. The reaction was then cooled to 0° C. and 2M HCl carefully added until the pH was acidic. The mixture was extracted using EtOAc (7×60 ml) and the organic extracts combined, dried (MgSO$_4$), filtered and concentrated in vacuo to give a yellow slurry. The crude residue was purified by flash chromatography (SiO$_2$) (7:3—EtOAc:Hexanes) to give the title compound (0.92 g, 11.62%) as a white solid. m/z (LC-MS, ESP): 197 [M−H]$^-$, R/T=0.52 mins.

Example 3b

Synthesis of 4-[1-(4,6-Di-morpholin-4-yl-[1,3,5]triazin-2-yl)-3H-imidazol-4-yl]-2,6-dimethoxy-phenol (17a)

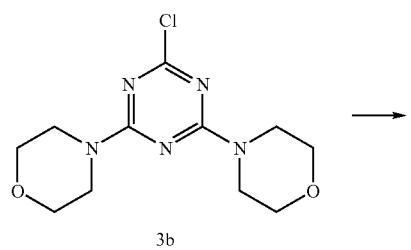

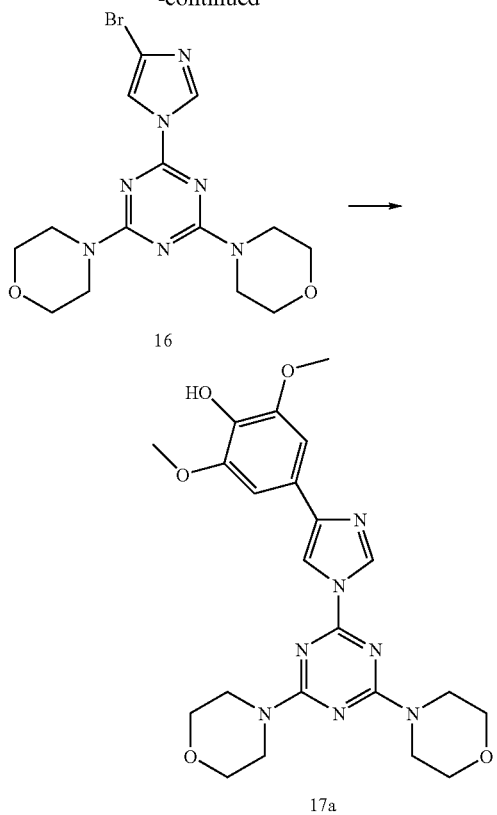

(i) 2-(4-Bromo-3H-imidazol-1-yl)-4,6-di-morpholin-4-yl-[1,3,5]triazine (16)

To a cooled solution of 4-bromo-1H-imidazole (0.249 g, 2.0 mmol) in anhydrous dimethylformamide (4 ml) was slowly added sodium hydride (60% dispersion in mineral oil) (0.088 g, 2.2 mmol). When the evolution of gas has ceased (30 mins), 2-chloro-4,6-di-morpholin-4-yl-[1,3,5]triazine (3b) (0.571 g, 2.00 mmol) was added in a single portion and the resulting mixture heated in a microwave reactor at 120° C. for exactly 14 minutes (fixed temperature holdtime, high absorbtion setting). The resulting brown/yellow slurry was diluted with water (10 ml) and filtered. The filter cake was washed with cold water (2×10 ml) and then dried in a vacuum dessicator to give the title compound in suitably pure form to be used without further purification. m/z (LC-MS, ESP): 396 [M+H]$^+$, R/T=3.61 mins.

(ii) 4-[1-(4,6-Di-morpholin-4-yl-[1,3,5]triazin-2-yl)-3H-imidazol-4-yl]-2,6-dimethoxy-phenol (17a)

To a microwave reaction vial containing a solution of 2-(4-Bromo-3H-imidazol-1-yl)-4,6-di-morpholin-4-yl-[1,3,5]triazine (16)(0.317 g, 0.80 mmol) in anhydrous dioxane (3 ml) was added tripotassium phosphate (0.34 g, 1.6 mmol) and 2,6-dimethoxy-phenol-4-boronic acid (15)(0.317 g, 1.6 mmol). The mixture was degassed for 5 minutes by sonicating and bubbling nitrogen through the solution before the addition of bis(tri-butylphosphine)palladium(0) The vial was sealed and heated while under the influence of microwave radiation at 170° C. for 11 minutes (fixed hold time). The crude reaction mixture was then filtered and the filter cake washed with methanol (10 ml). The solvent was removed in vacuo and the crude mixture submitted for purification using preparative HPLC to give the desired product. m/z (LC-MS, ESP): 470 [M−H]⁻, R/T=3.23 mins.

(iii) The following two compounds were made in an analgous fashion to compound 17a from compound 16:

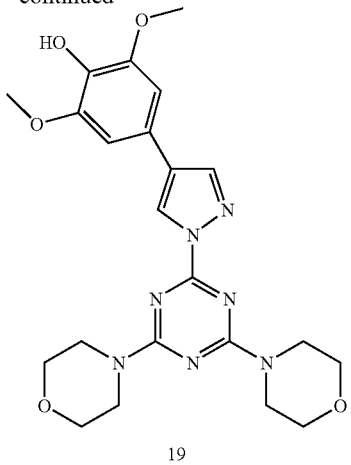

| | Ar | Purity % | m/z [M + H]⁺ | RT (mins) |
|---|---|---|---|---|
| 17b | (indole) | 98 | 433.0 | 3.23 |
| 17c | (isoquinoline) | 96 | 445.0 | 2.92 |

Example 3c

Synthesis of 4-[1-(4,6-Di-morpholin-4-yl-[1,3,5]triazin-2-yl)-1H-pyrazol-4-yl]-2,6-dimethoxy-phenol (19)

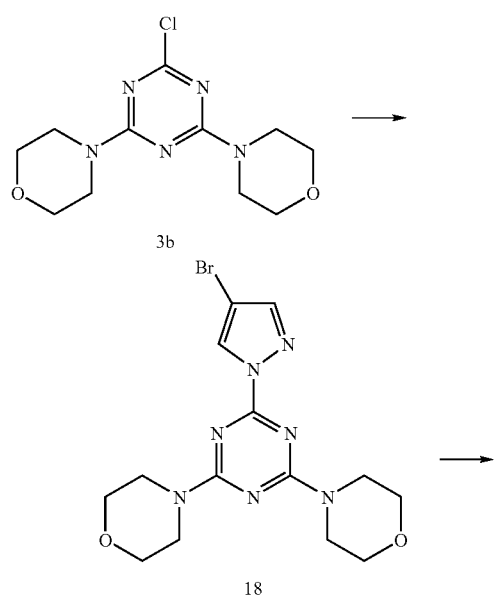

(i) 2-(4-Bromo-pyrazol-1-yl)-4,6-di-morpholin-4-yl-[1,3,5]triazine (18)

To a cooled (0° C.) solution of 4-bromopyrazole (0.29 g, 2.0 mmol) in anhydrous DMF (4 ml) was added NaH (60% dispersion in mineral oil, 0.088 g, 2.2 mmol) in a portionwise fashion over 10 minutes. The mixture allowed to warm to room temperature where it was stirred for 30 minutes before the adition of 2-Chloro-4,6-di-morpholin-4-yl-[1,3,5]triazine (3b)(0.571 g, 2.00 mmol). The mixture was then heated under the influence of microwave radiation (120° C., 14 minutes). Upon cooling the reaction was diluted with water (10 ml) and filtered. The filtercake was washed with more cold water (10 ml), collected and dried to give the title compound (92.4%, 0.73 g) in suitably pure form to be used without any further purification. m/z (LC-MS, ESP): 396 [M+H]⁺, R/T=3.56 mins.

(ii) 4-[1-(4,6-Di-morpholin-4-yl-[1,3,5] triazin-2-yl)-1H-pyrazol-4-yl]-2,6-dimethoxy-phenol (19)

This was synthesized by the coupling of (15) and (18) according to the method of Example 3b(ii). m/z (LC-MS, ESP): 470 [M−H]⁻, R/T=3.23 mins.

Example 3d

Synthesis of 2,6-Dimethoxy-4-[1-(4-morpholin-4-yl-pyrimidin-2-yl)-1H-pyrazol-4-yl]-phenol

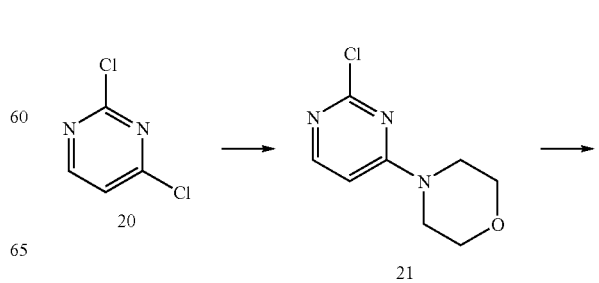

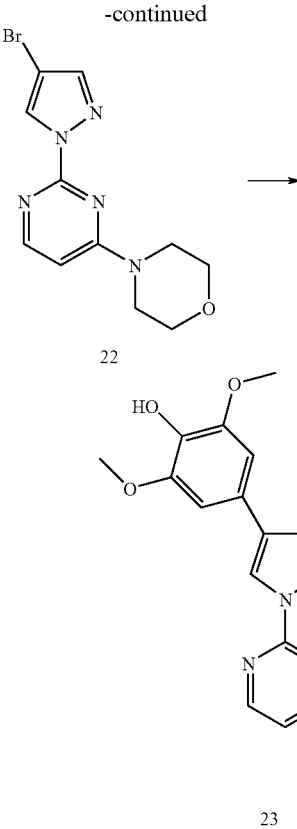

22

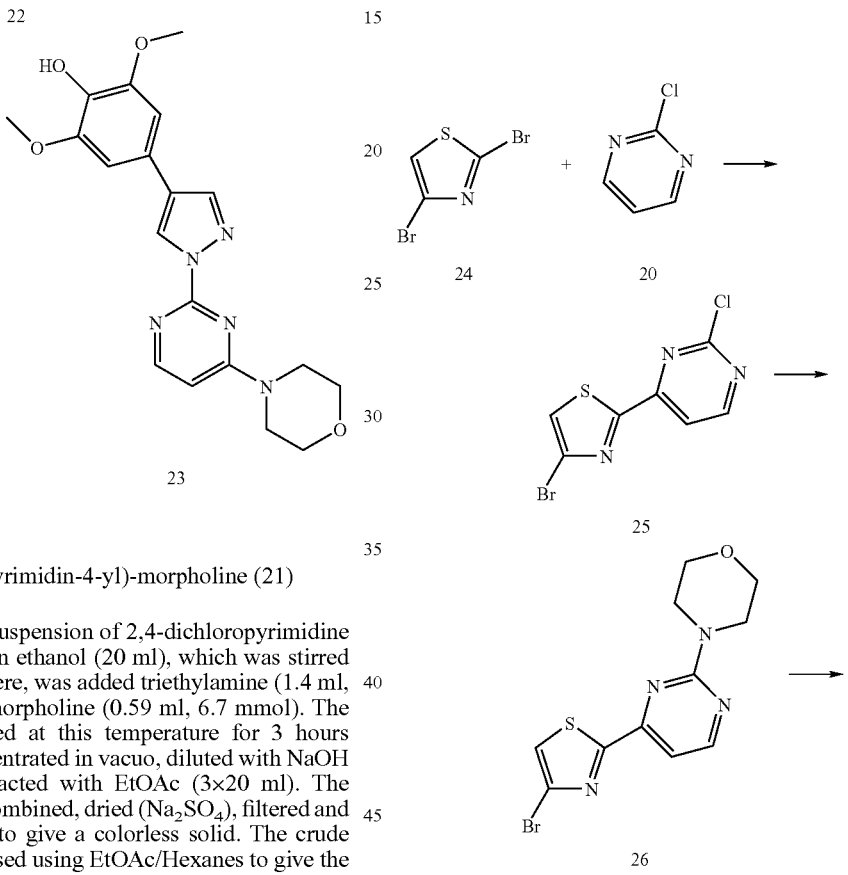

23

(i) 4-(2-Chloro-pyrimidin-4-yl)-morpholine (21)

To a cooled (0° C.) suspension of 2,4-dichloropyrimidine (20)(1.0 g, 6.7 mmol) in ethanol (20 ml), which was stirred under an inert atmosphere, was added triethylamine (1.4 ml, 10.1 mmol) and then morpholine (0.59 ml, 6.7 mmol). The mixture was maintained at this temperature for 3 hours whereupon it was concentrated in vacuo, diluted with NaOH (20 ml, 1M) and extracted with EtOAc (3×20 ml). The organic extracts were combined, dried ($Na_2SO_4$), filtered and concentrated in vacuo to give a colorless solid. The crude residue was re-crystallised using EtOAc/Hexanes to give the title compound (1.21 g, 90%) as a colourless solid which required no further purification. m/z (LC-MS, ESP): 200 $[M+H]^+$, R/T=3.26 mins

(ii) 4-[2-(4-Bromo-pyrazol-1-yl)-pyrimidin-4-yl]-morpholine (22)

To a cooled (0° C.) solution of 4-bromo-1H-pyrazole (0.74 g, 5.0 mmol) in anhydrous DMF (7 ml) was added NaH (60% dispersion in mineral oil, 0.22 g, 5.5 mmol) in a portionwise fashion over 10 minutes. The mixture was stirred like this for 30 minutes before the addition of 4-(2-chloro-pyrimidin-4-yl)-morpholine (21)(1.0 g, 5.00 mmol). The reaction was then heated under the influence of microwave radiation (120° C., 14 minutes, fixed hold time, high absorption setting). The reaction was then cooled to room temperature and water added (14 ml) which caused a precipitate to form. The solid was collected by filtration, washed with water and dried in a desiccator to give the title compound (1.44 g, 93%) in sufficiently pure form to be used without any further purification. m/z (LC-MS, ESP): 310 $[M+H]^+$, R/T=3.08 mins.

(iii) 2,6-Dimethoxy-4-[1-(4-morpholin-4-yl-pyrimidin-2-yl)-1H-pyrazol-4-yl]-phenol (23)

This was synthesized by the coupling of (15) and (18) according to the method of Example 3b(ii) to give a crude residue which was submitted for purification by preparative HPLC to give the desired product m/z (LC-MS, ESP): 470.4 $[M+H]^+$, R/T=3.23 mins.

Example 3e

Synthesis of 2,6-Dimethoxy4-[2-(2-morpholin-4-yl-pyrimidin4-yl)-thiazol-4-yl]-phenol (27)

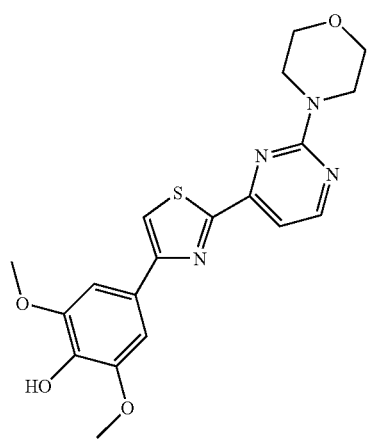

27

(i) 4-(4-Bromo-thiazol-2-yl)-2-chloro-pyrimidine (25)

To a cooled (−78° C.) solution of 2,4-dibromothiazole (24)(0.73 g, 3.0 mmol) in anhydrous diethylether (7 ml) was added n-butyllithium (2.5M in hexane, 1.5 ml, 3.28 mmol) in a dropwise fashion via syringe. The yellow solution was stirred at −78° C. for 15 minutes before the addition of a suspension of 2-chloropyrimidine (20)(2.73 mmol, 0.313 g) in anhydrous diethylether (8 ml). The mixture was allowed to warm to room temperature and maintained like this, with stirring for 16 hours. The mixture was quenched carefully by dropwise addition of water (0.061 ml, 3.41 mmol) in THF (0.7 ml) and then DDQ (0.681 g, 3.0 mmol) added to effect aromatization. The mixture was cooled to 0° C. and 3M NaOH$_{(aq)}$ (2.28 ml, 6.83 mmol) added which caused a sticky solid to adhere to bottom of the reaction vessel. The solvents were collected, dried (MgSO$_4$), filtered and concentrated in vacuo to give the title compound (0.58 g, 69.8%) in suitably clean form to be used without further purification. m/z (LC-MS, ESP): 327 [M+H]$^+$, R/T=3.73 mins.

(ii) 4-[4-(4-Bromo-thiazol-2-yl)-pyrimidin-2-yl]-morpholine (26)

To a solution of 4-(4-Bromo-thiazol-2-yl)-2-chloro-pyrimidine (25)(0.498 g, 1.8 mmol) in EtOH (8 ml) was added powdered potassium carbonate (0.274 g, 1.98 mmol) and morpholine (0.17 ml, 1.98 mmol). The mixture was heated under the influence of microwave radiation (10 minutes, 90° C., high absorption setting). The reaction mixture was then allowed to cool to room temperature and filtered through a thin pad of silica before being concentrated in vacuo. The crude residue was purified by flash chromatography (SiO$_2$) using Hexanes:EtOAc—(9:1) as eluent to give the title compound (0.18 g, 30.5%) in analytically pure form. m/z (LC-MS, ESP): 327 [M+H]$^+$, R/T=3.92 mins.

(iii) 2,6-Dimethoxy-4-[2-(2-morpholin-4-yl-pyrimidin-4-yl)-thiazol-4-yl]-phenol (27)

This was synthesized by the coupling of (15) and (26) according to the method of Example 3b(ii) to give a crude residue which was submitted for purification by flash chromatography (SiO$_2$) (eluent—9:1—MeOH:CH$_2$Cl$_2$) to give an orange solid (30.0%) in analytically pure form. m/z (LC-MS, ESP): 401.3 [M+H]$^+$, R/T=3.66

Example 3f

Synthesis of 2,6-Dimethoxy4-[1-(4-morpholin-4-yl-pyrimidin-2-yl)-1H-imidazol-4-yl]-phenol (29)

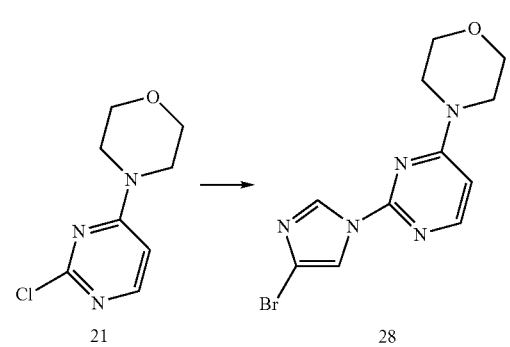

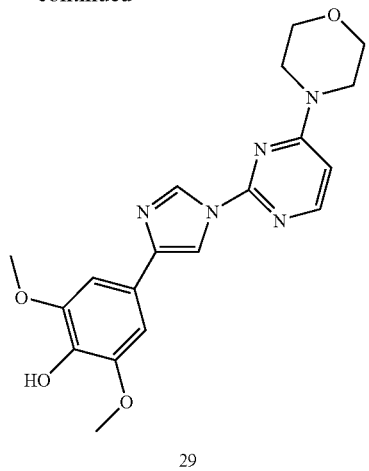

(i) 4-[2-(4-Bromo-imidazol-1-yl)-pyrimidin-4-yl]-morpholine (28)

To a cooled (0° C.) solution of 4-bromo-1-H-imidazole (0.8 g, 4.0 mmol) in anhydrous DMF (5.0 mmol) was added NaH (60% dispersion in mineral oil, 0.176 g, 4.4 mmol) in a portionwise fashion over 10 minutes. When gas evolution had ceased, 4-(2-Chloro-pyrimidin-4-yl)-morpholine (21)(0.79 g, 4.00 mmol) was added and the mixture heated under the influence of microwave radiation (120° C., 14 min, fixed hold time, pre-stirring 10 seconds, high absorption setting). Water (14 ml) was added to the reaction mixture which caused a precipitate to form. The precipitate was removed by filtration, washed with water (10 ml) and dried in a desiccator to give the title compound (1.17 g, 94.4%) in suitably clean form to be used without any further purification. m/z (LC-MS, ESP): 310 [M+H]$^+$, R/T=3.79 mins

(ii) 2,6-Dimethoxy-4-[1-(4-morpholin-4-yl-pyrimidin-2-yl)-1H-imidazol-4-yl]-phenol (29)

This was synthesized by the coupling of (15) and (28) according to the method of Example 3b(ii) to give a crude residue that was purified by preparative HPLC to give the title compound m/z (LC-MS, ESP): 384.4 [M+H]$^+$, R/T=2.80 mins.

Example 4

Synthesis of N-Methylene-N'-pyrido[3,4-d]pyramidin-4-yl-hydrazine Derivatives

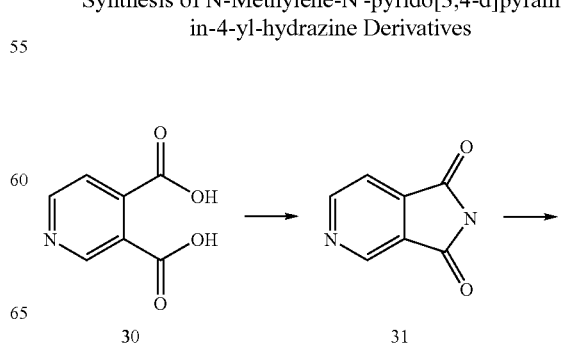

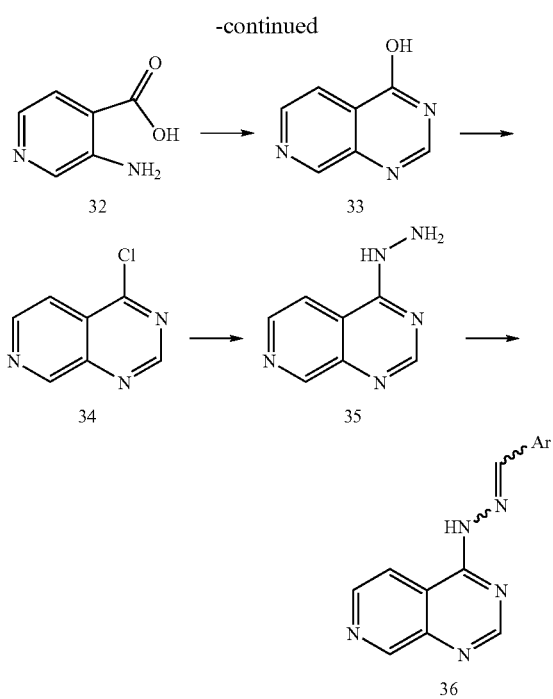

(i) Pyrrolo[3,4-c]pyridine-1,3-dione (31)

A suspension of cinchomeronic acid (30)(50 g, 300 mmol) in acetic anhydride (123.5 g, 1200 mmol) was heated to reflux (140-150° C.) until all solid material dissolved and the mixture was homogeneous. The mixture was then cooled and concentrated in vacuo. Acetamide (50 g, 846 mmol) was then added and the mixture heated to 140° C. for 3 hours whereupon it was then cooled to room temperature. The solid residue that formed upon cooling was pulverized and triturated with water (100 ml), filtered and washed with more water and dried in a desiccator to give the title compound (42.26 g, 95.1%) in suitably pure form to be used without any further purification. m/z (LC-MS, ESP): 149 [M+H]$^+$, R/T=0.44 mins.

(ii) 3-Amino-isonicotinic acid (32)

NaOH (10% aqueous, 640 ml) was cooled to 7° C. and bromine (15 ml, 286.82 mmol) added dropwise. Pyrrolo[3,4-c]pyridine-1,3-dione (41.711 g, 281.6 mmol) was then added to the reaction mixture before it was heated to 80° C. for 30 minutes. After this time the reaction was allowed to warm to 37° C. and the pH modified to 5.5 by the addition of acetic acid (70 ml). A suspension formed that was removed by filtration and washed with 20 ml of ice cold methanol to give the title compound (26.58 g, 68.33%) in a suitably clean form to be used without any further purification. m/z (LC-MS, ESP): 139 [M+H]$^+$, R/T=0.72 mins.

(iii) Pyrido[3,4-d]pyrimidin-4-ol (33)

A mixture of 3-amino-isonicotinic acid (32)(26.24 g, 190.0 mmol) and formamidine acetate (39.56 g, 380 mmol) in dimethylacetamide (100 ml) was stirred and heated to 150° C. The reaction was maintained at this temperature with stirring for 12 hours before it was allowed to cool to 25° C. and then basified with sodium bicarbonate solution (5% aqueous) until pH 7-8 was attained. The resultant pale brown solid was removed by filtration, washed with water (20 ml) and dried in a desiccator to give the desired compound (24.50 g, 87.63%) which required no further purification. m/z (LC-MS, ESP): 148 [M+H]$^+$, R/T=1.09 mins.

(iv) 4-Chloro-pyrido[3,4-d]pyrimidine (34)

A suspension of pyrido[3,4-d]pyrimidin-4-ol (33)(1.47 g, 10 mmol) in thionylchloride (30 ml) and dimethylformamide (50 μl, cat.) was heated to reflx (90° C.) for 1 hour. The mixture was then cooled and concentrated in vacuo and then diluted with CH$_2$Cl$_2$ (50 ml) which caused a suspension to form. The solid was removed by filtration, washed with cold CH$_2$Cl$_2$ (10 ml) to give the title compound (1.65 g, 99.4%) in sufficiently pure form to be used without any further purification. m/z (LC-MS, ESP): 166 [M+H]$^+$, R/T=2.82 mins.

(v) Pyrido[3,4-d]pyrimidin-4-yl-hydrazine (35)

To a suspension of 4-Chloro-pyrido[3,4-d]pyrimidine (34) (1.65 g, 10 mmol) in anhydrous THF (10 ml) was added hydrazine (1M in THF, 30 ml, 30 mmol). The reaction mixture was stirred at room temperature for 5 hours whereupon a yellow precipitate formed. The solid was removed by filtration, washed with cold THF (10 ml) and dried to give the title compound (1.56 g, 96.9%) as the sole product which required no further purification. m/z (LC-MS, ESP): 162 [M+H]$^+$, R/T=0.85 mins.

(vi) N-Methylene-N'-pyrido[3,4-d]pyramid in-4-yl-hydrazine Derivatives (36)

These were synthesized from 35 using the method of Example 1a(iv).

| Compound | Ar | Purity % | m/z [M + H]$^+$ | RT (mins) |
|---|---|---|---|---|
| 36a | 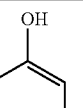 | 96 | 298 | 3.35 |
| 36b | 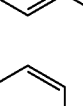 | 97 | 282 | 3.31 |
| 36c | 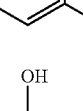 | 92 | 282 | 3.56 |
| 36d | 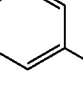 | 94 | 326 | 3.48 |

Example 5

Synthesis N-(6,7-Dimethoxy-quinazolin-4-yl)-N'-methylene-hydrazine Derivatives

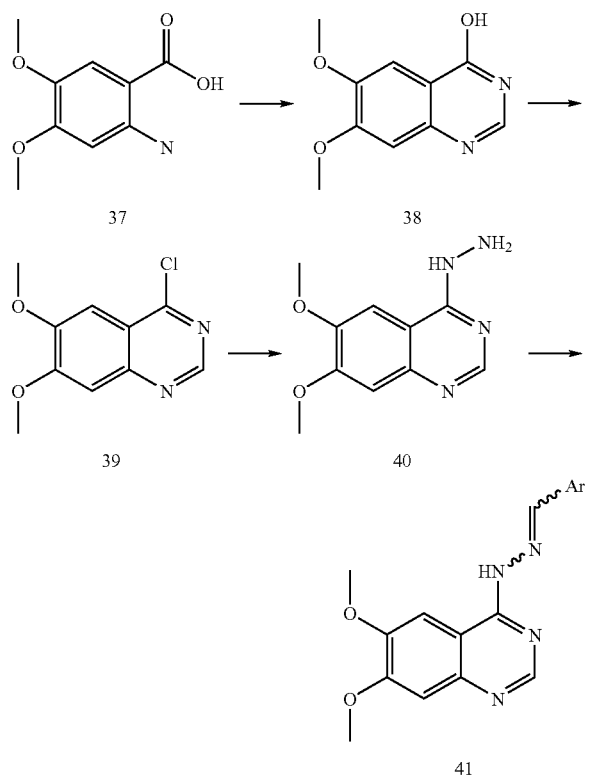

(i) 6,7-Dimethoxy-quinazolin-4-ol (38)

2-amino-4,5-dimethylbenzoic acid (37)(5 g, 25.30 mmol) and formamidine acetate (5.2 g, 50.00 mmol) were dissolved in 2-methoxyethanol (80 ml) and the mixture heated to reflux for 16 hours. The mixture was cooled and concentrated in vacuo and suspended in a small volume of water. Sodium bicarbonate (5% aqueous solution) was added carefully (gas evolution) until pH 7 was attained. The suspension was filtered and the filtercake washed with water to give the title compound (4.50 g, 86.2%) as a brown powder which required no further purification. m/z (LC-MS, ESP): 207 [M+H]$^+$, R/T=3.16 mins

(ii) 4-Chloro-6,7-dimethoxy-quinazoline (39)

To a suspension of 6,7-Dimethoxy-quinazolin-4-ol (1.65 g, 8.0 mmol) and phosporousoxychloride (1.52 ml, 16.4 mmol) in 1,2-dichloroethane (16 ml) was added diisopropylamine (3.48 ml, 20 mmol) in a dropwise fashion. The mixture was then heated to 80° C. under an inert atmosphere for 16 hours. After this time the reaction was cooled to room temperature and concentrated in vacuo to dryness, dissolved in $CH_2Cl_2$ (50 ml) and washed with sodium bicarbonate solution (5% aqueous, 2*25 ml). The organic layer was separated, dried using $MgSO_4$, filtered and concentrated in vacuo to give a brown residue that was purified by flash chromatography ($SiO_2$) eluted with $CH_2Cl_2$:EtOAc—2:98 then 5:95 to give the title compound (1.6 g, 88.9%) as a yellow solid. m/z (LC-MS, ESP): 207 [M+H]$^+$, R/T=3.51 mins

(iii) (6,7-Dimethoxy-quinazolin-4-yl)-hydrazine (40)

To a suspension of 4-Chloro-6,7-dimethoxy-quinazoline (0.20 g, 0.89 mmol) in anhydrous THF (0.5 ml) was added hydrazine (1M in THF, 2.0 ml, 2.0 mmol). The mixture was stirred at room temperature for 16 hours whereupon a precipitate had formed which was removed by filtration and washed with cold THF to give the desired product (177 mg, 91%) as a sticky off white solid which was sufficiently pure to be used without any further purification. m/z (LC-MS, ESP): 221 [M+H]$^+$, R/T=2.48 mins.

(iv) N-(6,7-Dimethoxy-quinazolin-4-yl)-N-methylene-hydrazine derivatives (41)

These were synthesised from 40 using the method of Example 1a(iv).

| Compound | Ar | Purity % | m/z [M + H]$^+$ | RT (mins) |
|---|---|---|---|---|
| 41a | HO-C$_6$H$_3$(OH)- (3,4-dihydroxyphenyl) | 100 | 341 | 3.28 |

Example 6

Synthesis of 4-[(3-morpholin-4-yl-phenyl)-hydrazonomethyl]-phenol derivatives

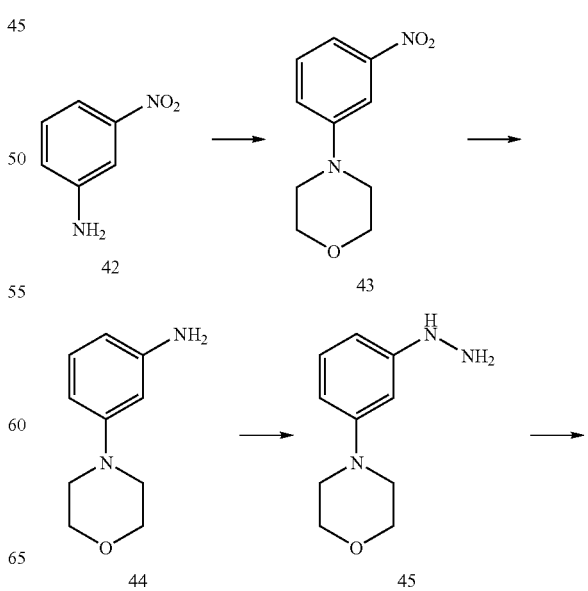

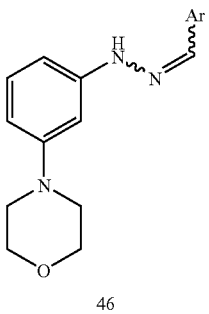

(i) 4-(3-Nitro-phenyl)-morpholine (43)

To a solution of 3-nitroaniline (42)(5.52 g, 40.00 mmol) in anhydrous dimethylacetamide (15 ml) was added 2-bromoethylether (7.52 ml, 60.00 mmol) and N,N-diisopropylethylamine (13.94 ml, 80.0 mmol). The mixture was then heated to 120° C. for 6 hours. After this time the reaction was cooled to room temperature which saw the mixture take the form of a slurry. The slurry was dissolved in $CH_2Cl_2$ (80 ml) and washed with 0.2 M HCl (3×30 ml). The organic layer was separated, dried ($MgSO_4$), filtered and concentrated in vacuo to give a brown semi-solid residue that was triturated with $Et_2O$ to give the desired product (8.33 g, 79.7%) in suitably clean form to be used without any further purification. m/z (LC-MS, ESP): 209 $[M+H]^+$, R/T=3.46 mins

(ii) 3-Morpholin-4-yl-phenylamine (44)

To a cooled (0° C.) solution of 4-(3-nitro-phenyl)-morpholine (43)(4.16 g, 20 mmol) in methanol (50 ml) was added Pd/C (10% loading, 460 mg). The mixture was stirred at room temperature under an $H_2$ (1 atm) for 16 hrs. The mixture was then filtered through a Celite™ pad, the filtrate dried using $MgSO_4$, filtered and concentrated in vacuo to give the title compound (3.39 g, 95.2%) as an orange solid that was suitably clean to be used without any further purification. m/z (LC-MS, ESP): 179 $[M+H]^+$, R/T=1.69 mins.

(iii) (3-Morpholin-4-yl-phenyl)-hydrazine (45)

To a cooled (−5 ° C.) solution of 3-morpholin-4-yl-phenylamine (44)(0.18 g, 1.00 mmol) in 2M $HCl_{(aq)}$ was added sodium nitrite (69 mg, 1.00 mmol in 1 ml water) dropwise. The red solution was stirred at −5° C. for 10 minutes before the addition of tin (II) chloride dihydrate (1.13 g, 5.0 mmol). The mixture was stirred vigorously and allowed to warm to room temperature over the period of 1 hour. 2M $NaOH_{(aq)}$ was added until the solution was basic (pH=8), then extracted with EtOAc (2×20 ml). The combined organic extracts were dried using $MgSO_4$, filtered and concentrated in vacuo to give the desired product (0.15 g, 79.0%) (3-Morpholin-4-yl-phenyl)-hydrazine. m/z (LC-MS, ESP): 194.4 $[M+H]^+$, R/T=1.00 mins.

(iv) 4-[(3-morpholin-4-yl-phenyl)-hydrazonomethyl]-phenol derivatives (46)

These were synthesized from 45 using the method of Example 1a(iv).

| Compound | Ar | Purity % | m/z $[M + H]^+$ | RT (mins) |
|---|---|---|---|---|
| 46a | (3,4,5-trihydroxyphenyl) | 90 | 330 | 2.81 |
| 46b | (4-hydroxy-3,5-dimethoxyphenyl) | 90 | 358 | 3.27 |

Example 7

Synthesis of 5-[(4,6-Di-morpholin-4-yl-[1,3,5]triazin-2-yl)-hydrazonomethyl] derivatives (47)

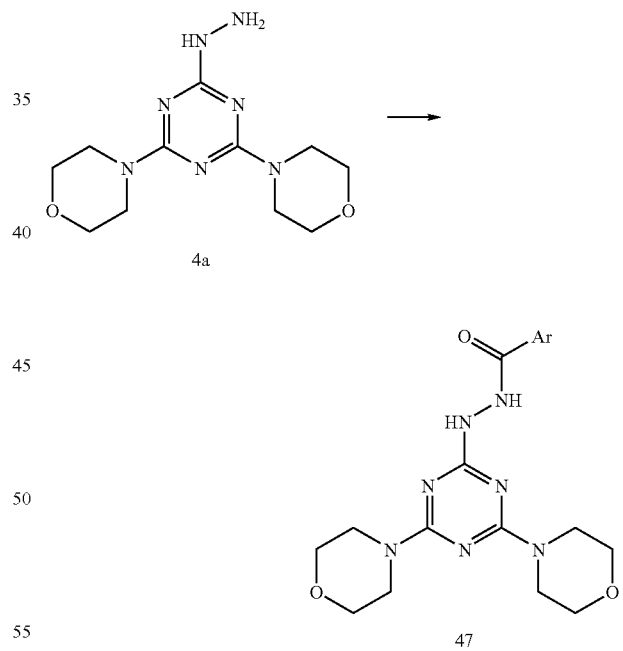

To a mixture of (4,6-Di-morpholin-4-yl-[1,3,5]triazin-2-yl)-hydrazine (4a)(0.02 g, 0.070 mmol) and the appropriate aromatic acid (47)(0.012 g, 0.070 mmol) in anhydrous DMA (0.5 ml) was added diisopropylethylamine (15 μl, 0.085 mmol) and then O-(7-Azabenzotriazol-1-yl)-N,N,N',N'-tetramethyluronium hexafluorophosphate (0.03 g, 0.08 mmol). The mixture was stirred at room temperature for 16 hours whereupon it was submitted for purification by preparative HPLC to give the desired product.

| Compound | Ar | Purity % | m/z [M + H]⁺ | RT (mins) |
|---|---|---|---|---|
| 47a | (3,4,5-trihydroxyphenyl) | 100 | 434 | 2.44 |
| 47b | (4-hydroxy-3,5-dimethoxyphenyl) | 90 | 462 | 2.68 |

Example 8

Synthesis of 2,6-Dimethoxy-4-[3-(2-morpholin-4-yl-pyrimidin-4-yl)-3H-imidazol-4-yl]-phenol (50)

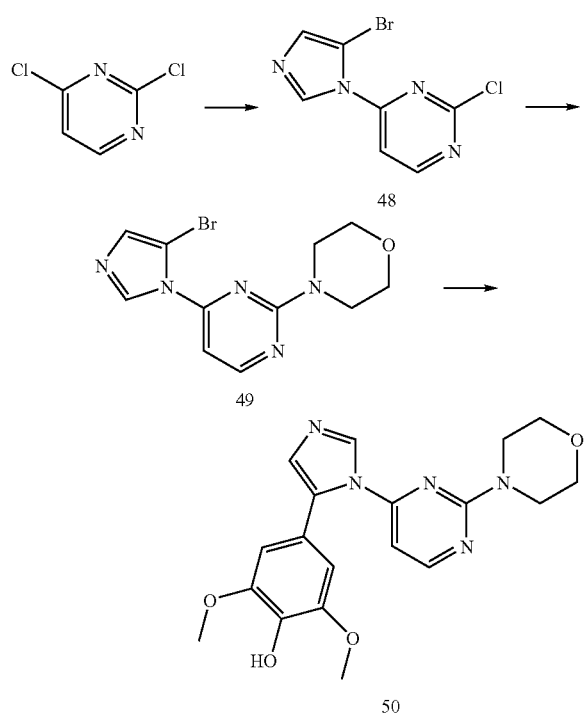

(i) 4-(5-Bromo-imidazol-1-yl)-2-chloro-pyrimidine (48)

To a solution of 2,4-dichloropyrimidine (0.447 g, 3 mmol) in anhydrous DMF (4 ml) was added potassium carbonate (0.415 g, 3 mmol). The reaction mixture was cooled (0° C.) under an inert atmosphere before the addition of 5-bromo-1-H-imidazole (0.441 g, 3 mmol) as solution in DMF (2 ml). The reaction was then allowed to stir at this temperature for a further 3 hours whereupon water (3 ml) was added. The resultant white precipitate was removed from the mixture by filtration and washed with water before being dried to give the title compound as a white solid (0.18 g, 23%) which was suitably pure to be used without further purification. m/z (LC-MSW, ESP):259.2,261.2 (bromine isotopes) [M+H]⁺, R/T=3.47 mins.

(ii) 4-[4-(5-Bromo-imidazol-1-yl)-pyrimidin-2-yl]-morpholine (49)

To a cooled (0° C.) solution of morpholine (0.256 g, 2.94 mmol) in anhydrouse DMF (5 ml) was added NaH (0.117 g, 2.94 mmol, 60% disp' in mineral oil). The mixture was stirred at this temperature for 30 minutes before the addition of 4-(4-Bromo-imidazol-1-yl)-2-chloro-pyrimidine (0.64 g, 2.45 mmol). The reaction vessel was sealed and heated under the infuenceof microwave radiation for 7 minutes (120° C., High absorption setting). Upon cooling the mixture was diluted with water (7 ml) and the resultant yellow precipitate removed by filtration and purified by flash chromatography (SiO₂) (4:1—Hexanes:EtOAc) to give the title compound as a white solid in analytically (0.76 g, 38.6%) pure form. m/z (LC-MSW, ESP):310.2 [M+H]⁺, R/T=3.21 mins.

(iii) 2,6-Dimethoxy-4-[3-(2-morpholin-4-yl-pyrimidin-4-yl)-3H-imidazol-4-yl]-phenol (50)

To a solution of 4-[4-(4-Bromo-imidazol-1-yl)-pyrimidin-2-yl]-morpholine (0.20 g, 0.65 mmol) in anhydrous dioxane (6 ml) and anhydrous DMA (0.6 m) was added tripotassium phosphate (0.28 g, 1.3 mmol) and 2,6-dimethoxy-phenol-boronic acid (0.18 g, 0.91 mmol). The resultant mixture was degassed with sonication for 10 minutes before the addition of bis(tri-butylphospine)palladium (0.017 g, 0.033 mmol) and degassing for a further 5 minutes. The reaction vessel was sealed and heated under the influence of microwave radiation (170° C., 11 min, low absorption setting). Upon completion, the reaction was filtered through a thin silica plug which was then washed with 10% methanol/CH₂Cl₂. The filtrate was concentrated in vacuo and the crude residue purified by flash chromatography (SiO₂) (1:1—EtOAc:Hexanes) to give the desired product (0.24 g, 96%) as a white crystalline solid in analytically pure form. m/z (LC-MSW, ESP):384.4 [M+H]⁺, R/T=2.90 mins.

Example 9

Synthesis of 2,6-Dimethoxy-4-[1-(2-morpholin-4-yl-pyrimidin4-yl)-1H-imidazol-4-yl]-phenol (53)

-continued

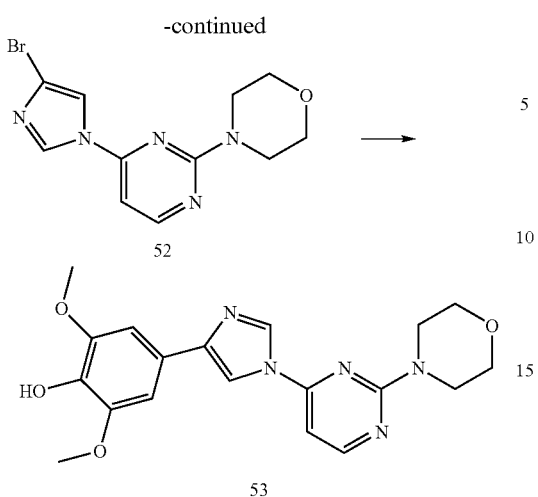

(i) 4-(4-Bromo-imidazol-1-yl)-2-chloro-pyrimidine (51)

To a solution of 2,4-dichloropyrimidine (0.447 g, 3 mmol) in anhydrous DMF (4 ml) was added potassium carbonate (0.415 g, 3 mmol). The reaction mixture was cooled (0° C.) under an inert atmosphere before the addition of 4-bromo-1-H-imidazole (0.441 g, 3 mmol) as solution in DMF (2 ml). The reaction was then allowed to stir at this temperature for a further 3 hours whereupon water (3 ml) was added. The resultant white precipitate was removed from the mixture by filtration and washed with water before being dried to give the title compound as a white solid (0.18 g, 23%) which was suitably pure to be used without further purification. m/z (LC-MSW, ESP):259.2,261.2 (bromine isotopes) [M+H]$^+$, R/T=3.47 mins.

(ii) 4-[4-(4-Bromo-imidazol-1-yl)-pyrimidin-2-yl]-morpholine (52)

To a cooled (0° C.) solution of morpholine (0.256 g, 2.94 mmol) in anhydrouse DMF (5 ml) was added NaH (0.117 g, 2.94 mmol, 60% disp' in mineral oil). The mixture was stirred at this temperature for 30 minutes before the addition of 4-(4-Bromo-imidazol-1-yl)-2-chloro-pyrimidine (0.64 g, 2.45 mmol). The reaction vessel was sealed and heated under the infuenceof microwave radiation for 7 minutes (120° C., High absorption setting). Upon cooling the mixture was diluted with water (7 ml) and the resultant yellow precipitate removed by filtration and purified by flash chromatography (SiO$_2$) (4:1—Hexanes:EtOAc) to give the title compound as a white solid in analytically (0.76 g, 38.6%) pure form. m/z (LC-MSW, ESP):310.3 [M+H]$^+$, R/T=3.26 mins.

(iii) 2,6-Dimethoxy-4-[3-(2-morpholin-4-yl-pyrimidin-4-yl)-3H-imidazol-4-yl]-phenol (53)

To a solution of 4-[4-(4-Bromo-imidazol-1-yl)-pyrimidin-2-yl]-morpholine (0.20 g, 0.65 mmol) in anhydrous dioxane (6 ml) and anhydrous DMA (0.6 m) was added tripotassium phosphate (0.28 g, 1.3 mmol) and 2,6-dimethoxy-phenol-boronic acid (0.18 g, 0.91 mmol). The resultant mixture was degassed with sonication for 10 minutes before the addition of bis(tri-butylphospine)palladium (0.017 g, 0.033 mmol) and degassing for a further 5 minutes. The reaction vessel was sealed and heated under the influence of microwave radiation (170° C., 11 min, low absorption setting). Upon completion, the reaction was filtered through a thin silica plug which was then washed with 10% methanol/CH$_2$Cl$_2$. The filtrate was concentrated in vacuo and the crude residue purified by flash chromatography (SiO$_2$) (1:1—EtOAc:Hexanes) to give the desired product (0.24 g, 96%) as a white crystalline solid in analytically pure form. m/z (LC-MSW, ESP):384.4 [M+H]$^+$, R/T=2.72 mins.

Example 10

Synthesis of 2-[N'-Ethylidene-hydrazino]-pyrimidin-4-ylamine derivatives (56)

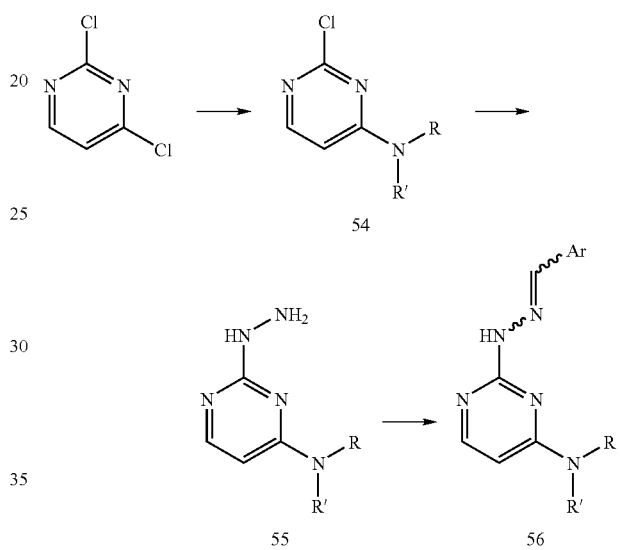

(i) 2-Chloro-pyrimidin-4-ylamine derivatives (54)

To a cooled (0° C.) suspension of 2,4-dichloropyrimidine (10 g, 67.6 mmol) and potassium carbonate (9.3 g, 67.6 mmol) in anhydrous DMA (45 ml) was added the appropriate amine (1 equiv, 67.6 mmol) in a dropwise fashion over 30 minutes. The mixture was then maintained at this temperature for a further 3 hours whereupon it was poured carefully onto crushed ice. The resultant white precipitate was removed by filtration and washed with water to give the desired adduct.

54a: NRR'=morpholino: m/z (LC-MSW, ESP):200.4 [M+H]$^+$, R/T=3.98 mins.

(ii) 2-Hydrazino-pyrimidin-4-ylamine derivatives (55)

To a solution of the appropriate 2-Chloro-pyrimidin-4-ylamine derivative (1 equiv, 46.1 mmol) in ethanol (45 ml) was added hydrazine hydrate (7.2 ml, 231 mmol). The mixture was heated to 90° C. under an inert atmosphere for 4 hours. The reaction was then cooled to 0° C. and the resultant precipitate collected by filtration. The collected product was washed with cold water and recrystallised from the minimum quantity of hot ethanol to give the desired product in suitably clean form to be used without further purification.

55a: NRR'=morpholino: m/z (LC-MSW, ESP):195.4 [M+H]$^+$, R/T=0.37 mins.

(iii) 2-[N'-arylylidene-hydrazino]-pyrimidin-4-ylamine derivatives (56)

To a solution of the appropriate of 2-Hydrazino-pyrimidin-4-ylamine derivative (1 equiv, 0.26 mmol) in ethanol was added p-toluenesulfonic acid (0.05 equiv, 0.013 mmol) and the appropriate aldehyde (1.2 equiv, 0.30 mmol). The reaction vessel was sealed and heated under the influence of microwave radiation (10 minutes, 130° C., high absorption setting). The reaction was cooled and filtered. The filtrant was washed with cold ethanol to give a white solid which corresponded to the desired product.

sion of 2-chloropyrimidine (0.85 g, 7.5 mmol) in anhydrous diethylether (15 ml) was added slowly and the resulting solution allowed to slowly warm up to room temperature. The misture was then allowed to stir at room temperature for 1 hr before being quenched with water (0.113 ml, 5.0 mmol) in THF (1.25 ml) and treated with DDQ (1.25 g, 5.4 mmol) in THF (6.25 ml). The mixture was then stirred at 25° C. for 15 minutes, cooled to 0° C., treated with hexanes (4.16 ml) then cold 2M NaOH (6.25 ml, 12.5 mmol). The organic extract was removed and remaing aqueous fraction extracted further with $CH_2Cl_2$ (3×20 ml). The organic extracts were combined, dried ($MgSO_4$), filtered and concentrated in vacuo to give a

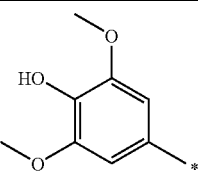

sticky brown residue which was purified by flash chromatography ($SiO_2$) (1:1—$CH_2Cl_2$:Hexanes going to 7:3—$CH_2Cl_2$:Hexanes) to give a white solid (1.38 g, 47.1%) corresponding to the title compound in analytically pure form. m/z (LC-MSW, ESP):278.0 $[M+H]^+$, R/T=3.90 mins (ii) 2-Chloro-4-(4-aryl-thiazol-2-yl)-pyrimidine derivatives (58)

To a solution of Synthesis of 4-(4-Bromo-thiazol-2-yl)-2-chloro-pyrimidine (0.2 g, 1 eq) in anhydrous dioxane (8 ml) was added the appropriate boronic acid or ester (3.2 eq) and tripotassium phosphate (4 equiv). The mixture was degassed with sonication for 10 minutes before bis(tri-butylphosphine) palladium (0.05 equiv) was added. The resulting solution was degassed with sonication for a further 10 minutes. The reaction vessel was then sealed and heated under the influence of microwave radiation (130° C., 1 hour, medium absorption setting). Upon cooling, the reaction mixture was concentrated in vacuo to give a sticky oil which was then purified by flash chromatography ($SiO_2$) (7:3—$CH_2Cl_2$:Hexanes going to 99:1—$CH_2Cl_2$:MeOH) to give the desired compound in analytically pure form.

(iii) 4-(4-aryl-thiazol-2-yl)-pyrimidin-2-ylamine derivatives (59)

To a solution of the appropriate chloropyrimidine derivative (1 equiv, 0.14 mmol) in ethanol (2 ml) was added potassium carbonate (2.1 equiv) and the appropriate amine (1.1 equiv). The reaction vessel was sealed and heated under the influence of microwave radiation (90° C., 10 minutes, high absorption setting). The crude reaction was then filtered through a thin silica pad before being purified by preparative HPLC to give the desired products.

Example 11

Synthesis of 4-(4-aryl-thiazol-2-yl)-pyrimidin-2-ylamine derivatives (59)

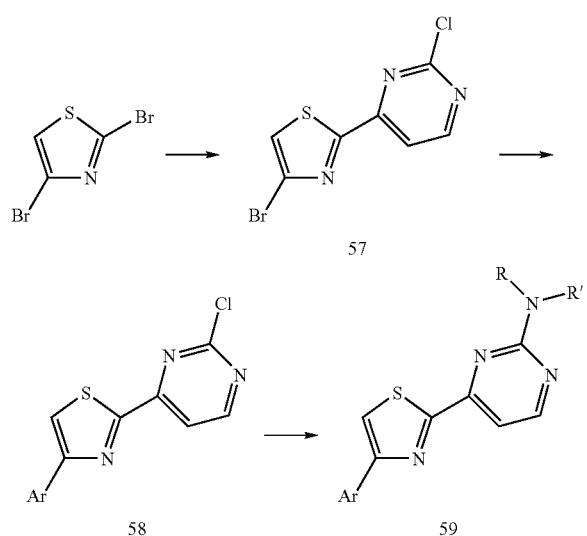

(i) 4-(4-Bromo-thiazol-2-yl)-2-chloro-pyrimidine (57)

To a cooled (−78° C.) solution of 2,4-dibromothiazole (1.22 g, 5.0 mmol) in anhydrous diethyl ether (15 ml) was added n-Butyllithium (2.2 ml of 2.5 M solution in Hexanes, 5.5 mmol) in a dropwise fashion. The mixture was maintained at this temperature, with stirring, for 1 hour before a suspen-

| Compound | NRR' | Ar | Purity % | m/z [M + H]+ | RT (mins) |
|---|---|---|---|---|---|
| 59a | *-N(morpholine) | 2,6-difluoro-4-*-phenol | 99 | 377.2 | 3.94 |
| 59b | *-N(4-hydroxypiperidine) | 3,5-dimethoxy-4-hydroxy-phenyl-* | 99 | 415.3 | 3.33 |
| 59c | *-N(3-hydroxypiperidine) | 3,5-dimethoxy-4-hydroxy-phenyl-* | 99 | 415.3 | 3.45 |
| 59d | *-N(2,6-dimethylmorpholine) | 3,5-dimethoxy-4-hydroxy-phenyl-* | 99 | 429.0 | 4.85 |
| 59e | *-N(3-hydroxypyrrolidine) | 3,5-dimethoxy-4-hydroxy-phenyl-* | 99 | 401.0 | 3.68 |
| 59f | *-N(homomorpholine) | 3,5-dimethoxy-4-hydroxy-phenyl-* | 99 | 415.0 | 4.43 |
| 59g | *-N(morpholine) | 3-(hydroxymethyl)phenyl-* | 99 | 355 | 4.39 |
| 59h | *-N(4-hydroxy-2-carboxypyrrolidine) | 3,5-dimethoxy-4-hydroxy-phenyl-* | 89 | 445 | 3.43 |

-continued

| Compound | NRR' | Ar | Purity % | m/z [M + H]+ | RT (mins) |
|---|---|---|---|---|---|
| 59i | 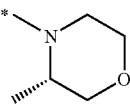 | 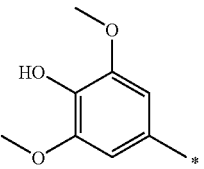 | 95 | 415.0 | 4.72 |
| 59j | 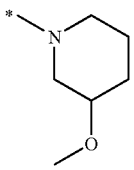 | 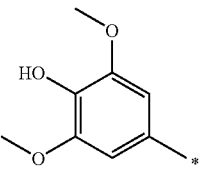 | 99 | 429 | 4.86 |

Example 12

Synthesis of 4-(5-aryl-furan-2-yl)-pyrimidin-2-ylamine derivatives (62)

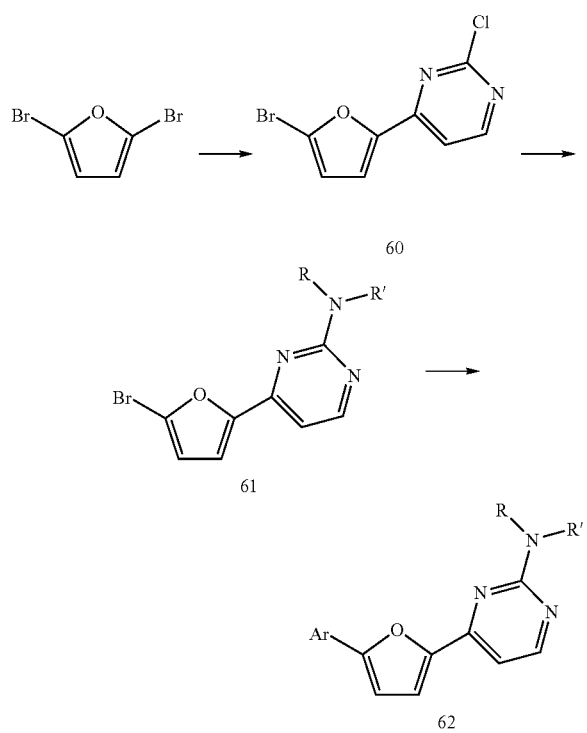

(i) 4-(5-Bromo-furan-2-yl)-2-chloro-pyrimidine (60)

To a cooled (−78° C.) solution of 2,5-dibromofurane (3.06 g, 8.88 mmol) in anhydrous diethyl ether (50 ml) was added n-Butyllithium (3.9 ml of 2.5M solution in Hexanes, 9.77 mmol). The mixture was stirred at this temperature for 90 minutes before the addition of 2-chloropyrimidine. The mixture was stirred for a further 30 minutes before being warmed to room temperature and stirred for further 2 hours. DDQ (2 g, 8.88 mmol) was them added to the solution which was stirred for 30 minutes before being concentrated in vacuo to give a thick brown syrup. The syrup was dissolved in EtOAc and washed with saturated sodium carbonated solution. The organic extract was removed, dried (MgSO$_4$), filtered and concentrated in vacuo to give a crude residue which was purified by flash chromatography (SiO$_2$) (100% hexane going to 7:2—hexane:EtOAc) to give the title compound (3.06 g, 40.20%) in pure form. m/z (LC-MSW, ESP):346 [M+H]+, R/T=4.41 mins (ii) 4-(5-Bromo-furan-2-yl)-pyrimidin-2-ylamine derivatives (61)

To a solution of 4-(5-Bromo-furan-2-yl)-2-chloro-pyrimidine (1.23 g, 4.74 mmol) in ethanol (60 ml) was added the appropriate amine (2.5 equiv). The mixture was heated to 70° C. for 10 hrs before being cooled, and concentrated in vacuo to give a slurry. The residue was dissolved in EtOAc (100 ml) and washed with water (100 ml). The organic extract was separated, and dried (MgSO$_4$) before being filtered and concentrated in vacuo to give the desired product in suitably clean form to be used without further purification.

61a: NRR'=morpholino: m/z (LC-MSW, ESP):310 [M+H]+, R/T=3.33 mins (iii) 4-(5-aryl-furan-2-yl)-pyrimidin-2-ylamine derivatives (62)

To a solution of the appropriate 4-(5-Bromo-furan-2-yl)-pyrimidin-2-ylamine derivative (1 equiv, 0.081 mmol) in anhydrous dioxane modified with 10% DMF (1.5 ml total) was added tripotassium phosphate (2 eq). The solution was degassed with sonication for 10 minutes prior to the addition of bis(tri-butylphosphine)palladium (0.06 equivs) and degassing, with sonication, for a further 5 minutes. The reaction vessel was then sealed and heated under the influence of microwave radiation (26 minutess, 170° C., medium absorption setting). The mixture was cooled, and filtered through a silica plug, concentrated in vacuo and purified by preparative HPLC to give the desired products.

| Compound | NRR' | Ar | Purity % | m/z [M + H]+ | RT (mins) |
|---|---|---|---|---|---|
| 62a | *−N(morpholine) | HO, 2,6-dimethoxyphenyl-* | 87 | 400 | 4.31 |

Example 13

Synthesis of 4-(5-aryl-furan-2-yl)-2,6-dimorpholino-pyrimidine derivatives (66)

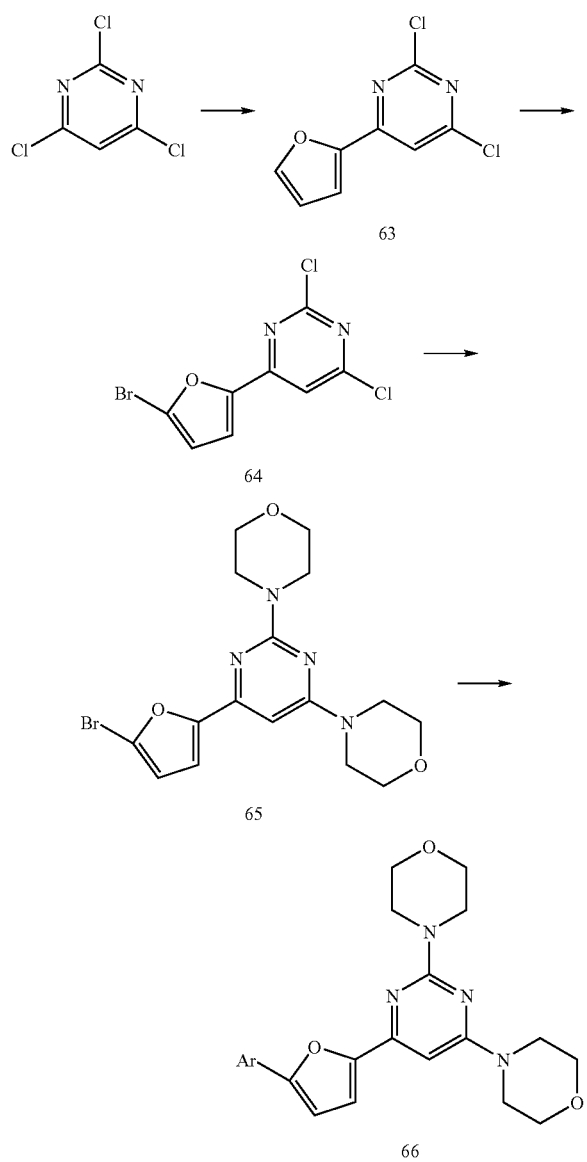

(i) 2,4-Dichloro-6-furan-2-yl-pyrimidine (63)

To a solution of 2,4,6-trichloropyrimidine (0.5 g, 2.73 mmol), 2-furanboronic acid (0.152 g, 1.36 mmol), potassium carbonate (0.377 g, 1.36 mmol)) in toluene (2.5 ml) was added tetrakis(triphenylphosphine)palladium (0.08 g, 0.068 mmol). The reaction vessel was sealed and heated under the influence of microwave radiation (130° C., 600 seconds, low absorption setting). The crude reaction was concentrated in vauo to give an orange oil which was purified by flash chromatography (SiO$_2$) (19:1—Hexanes:EtOAc) to give the title compound (342 mg, 58%) in suitably clean form to be used without further purification. m/z (LC-MSW, ESP):215.1 [M+H]+, R/T=4.68 mins (ii) 4-(5-Bromo-furan-2-yl)-2,6-dichloro-pyrimidine (64)

To a stirred solution of 2,4-Dichloro-6-furan-2-yl-pyrimidine (1.44 g, 6.71 mmol) in DMF (20 ml) was added N-bromosuccinimide (1.31 g, 7.38 mmol) in a portionwise fashion. The resultant mixture was stirred at room temperature for a 2.5 hours before being diluted in EtOAc (50 ml) and washed with water (2×50 ml). The organic extract was dried (MgSO$_4$), filtered and concentrated in vacuo to give an orange, semi-crystalline slurry. The crude residue was washed with ether and filtered to leave the desired product (1.29 g, 99%) as a whited crystalline solid in suitably clean form to be used without any further purification. m/z (LC-MSW, ESP):294 [M+H]+, R/T=5.09 mins.

(iii) 4-(5-bromo-furan-2-yl)-2,6-dimorpholino-pyrimidine (65)

To a solution of 4-(5-Bromo-furan-2-yl)-2,6-dichloro-pyrimidine (1.93 g, 6.51 mmol) in DMA (35 ml) was added morpholine (2.83 g, 32.54 mmol) and N,N-diisopropylethylamine (4.21 g, 32.54 mmol). The reaction mixture was heated to 70° C. for 7 hours whereupon it was cooled and diluted with EtOAc (100 ml) and then washed with water (2×50 ml), dried (MgSO$_4$), filtered and concentrated in vacuo to give a dark oil. The crude residue was purified by flash chromatography (SiO$_2$) (1:3—EtOAc:Hexanes) to give the title compound as a white crystalline solid (0.95 g, 37%). m/z (LC-MSW, ESP):396 [M+H]+, R/T=4.38 mins.

(iv) 4-(5-aryl-furan-2-yl)-2,6-dimorpholino-pyrimidine derivatives (66)

To a solution of 4-(5-bromo-furan-2-yl)-2,6-dimorpholino-pyrimidine (0.03 g, 0.076 mmol) in dioxane (2 ml) were added 2 drops of water, the appropriate boronic acid (1.2 equiv), tripotassium phosphate (1.2 equiv) and bis(tris-t-butylphosphine)palladium (0.05 equiv). The reaction vessel was sealed and heated under the influence of microwave radiation (150° C., 600 s, medium absorption setting). The reaction was then diluted in EtOAc (5 ml), washed with water (2 ml) and then brine (2 ml). the organic extract was removed, filtered through a silica plug, concentrated in vacuo and purified by preparative HPLC to give the desired compounds.

| Compound | Ar | Purity % | m/z [M + H]$^+$ | RT (mins) |
|---|---|---|---|---|
| 66a | (3,4-dimethoxy-hydroxyphenyl) | 95 | 469.3 | 8.57 |
| 66b | (hydroxymethyl-methoxyphenyl) | 98 | 453.4 | 8.56 |
| 66c | (pyridin-4-yl) | 100 | 394.3 | 6.49 |
| 66d | (3-hydroxymethylphenyl) | 100 | 4223 | 3.83 |
| 66e | (4-hydroxymethylphenyl) | 97 | 423.3 | 4.42 |
| 66f | (3-hydroxyphenyl) | 100 | 409 | 3.91 |
| 66g | (4-hydroxyphenyl) | 99 | 409.4 | 4.47 |
| 66h | (2-fluorophenyl) | 96 | 489 | 3.98 |

Example 14

Synthesis of 4-(4-aryl-thiophen-2-yl)-pyrimidin-2-ylamine derivatives (69)

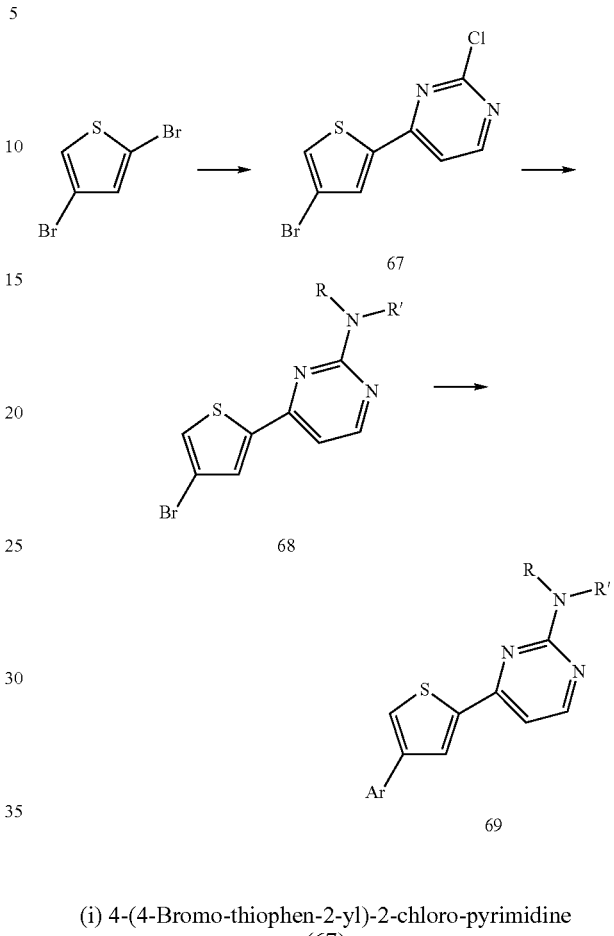

(i) 4-(4-Bromo-thiophen-2-yl)-2-chloro-pyrimidine (67)

To a cooled (−78° C.) solution of 2,4-dibromothiophene (1 g, 4.13 mmol) in diethylether (30 ml) was added n-butyl lithium (2.5M in Hexanes, 4.55 mmol, 1.82 ml). The solution was maintained at this temperature for 1 hour before the addition of 2-chloropyrimidine (0.47 g, 4.13 mmol) in a single portion. The mixture was maintained at −78° C. for a further 1.5 hours before being allowed to warm up to room temperature. Ethyl acetate (20 ml) was added followed by DDQ (0.94 g, 4.13 mmol). The reaction was stirred for a further 30 minutes before being concentrated in vacuo. The crude residue was purified by flash chromatography (SiO$_2$) (7:3—Hexanes:EtOAc) to give the desired product (0.42 g, 37%) as a pale yellow solid which corresponded to the title compound. m/z (LC-MSW, ESP):275 [M+H]$^+$, R/T=4.72 mins.

(ii) 4-(4-Bromo-thiophen-2-yl)-pyrimidin-2-ylamine derivatives (68)

A solution of 4-(4-Bromo-thiophen-2-yl)-2-chloro-pyrimidine (1 equiv, 1.20 mmol) in ethanol (30 ml) was stirred at room temperature and to this solution was added the appropriate amine (5 equiv). The mixture was heated 70° C. for 16 hours. Upon cooling the reaction was concentrated in vacuo to give a slurry which was dissolved in EtOAc (150 ml) and washed with saturated sodium bicarbonate solution (100 ml).

The organic extract was separated, dried (MgSO₄), filtered and concentrated in vacuo to give the desired compound in suitably cean form to be used without any further purification.

68a: NRR'=morpholino: m/z (LC-MSW, ESP):326 [M+H]⁺, R/T=4.93 mins.

(iii) 4-(4-aryl-thiophen-2-yl)-pyrimidin-2-ylamine derivatives (69)

To a solution of the appropriate 4-(4-Bromo-thiophen-2-yl)-pyrimidin-2-ylamine derivative (1 equiv, 0.08 mmol) in 1:1-toluene:Ethanol (5 ml) was added tetrakis(triphenylphosphine)palladium (0.05 equiv), sodium carbonate (2 equiv) and the appropriate boronic acid (1 equiv). The reaction mixture was heated under the influence of microwave radiation (140° C., 30 minutes, medium absorption setting), cooled, filtered through a thin silica plug, concentrated in vacuo and purified by preparative HPLC to give the desired compound.

| Compound | NRR' | Ar | Purity % | m/z [M + H]⁺ | RT (mins) |
|---|---|---|---|---|---|
| 69a | morpholino | 4-hydroxy-3,5-dimethoxyphenyl | 100 | 400.0 | 4.31 |

Example 15

Synthesis of 2-{N-Methyl-N'-[1-Aryl-methylidene]-hydrazino}-pyrido[2,3-d]pyrimidin-4-ylamine derivatives (75)

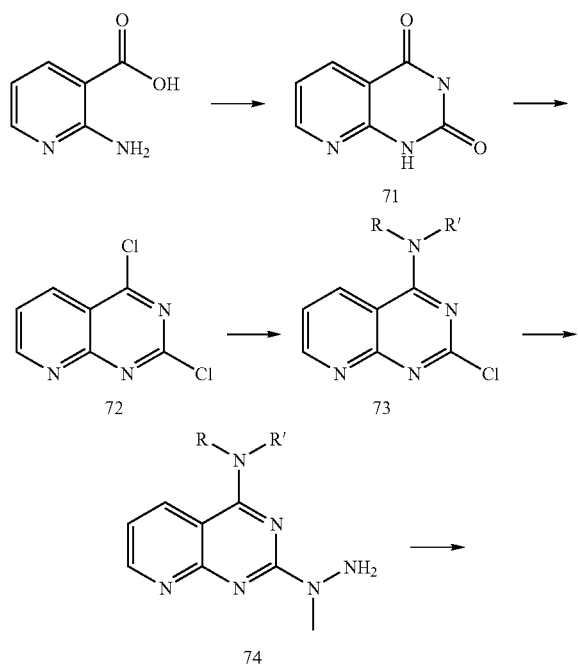

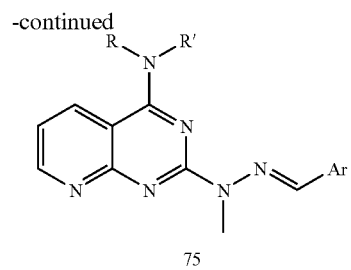

(i) 1H-Pyrido[2,3-d]pyrimidine-2,4-dione (71)

A slurry of 2-aminonicotinic acid (10 g, 72.5 mmol), ammonium chloride (39 g, 725 mmol) and potassium cyanate (30 g, 362 mmol) in water (80 ml) was heated to 80° C. and maintained at this temperature with stirring for 30 minutes before being heated to 200° C. The mixture was stirred for 2 hours at this elevated temperature and then left to cool. Water (200 ml) was then added and the resultant mixture filtered. The solid was washed with hot water (100 ml) and then with cold water (2×100 ml) to give a yellow solid which corresponded to the title compound (11.79 g, 99%) in suitably clean form to be used without any further purification. m/z (LC-MSW, ESP):164 [M+H]⁺, R/T=2.11 mins.

(ii) 2,4-Dichloro-pyrido[2,3-d]pyrimidine (72)

To a solution of 1H-Pyrido[2,3-d]pyrimidine-2,4-dione (5.0 g, 30.65 mmol) in toluene (50 ml), under an inert atmosphere, was added N,N-diiospropylethylamine (19.81 g, 153.2 mmol). Phosporous oxychloride (23.50 g, 153.2 mmol) was then added to the mixture dropwise before the reaction was heated to 100° C. for 3 hours. The mixture was then concentrated in vacuo and then diluted in CH₂Cl₂ (200 ml) before being poured carefully into ice water (300 ml). The biphasic mixture was then filtered through a thin pad of Celite™, neutralized and separated. The aqueous phase was extracted further with CH₂Cl₂ (2×100 ml) and the combined organic extract dried (sodium sulfate), filtered and concentrated in vacuo to give a thick syrup which was used in it crude form for the next step.

(iii) 2-Chloro-pyrido[2,3-d]pyrimidin-4-ylamine derivatives (73)

Crude 2,4-Dichloro-pyrido[2,3-d]pyrimidine (6.66 g, 33.47 mol) was diluted in anhydrous THF (50 ml) under an inert atmosphere. To this was slowly added the appropriate amine (0.8 equiv) and the resultant mixture stirred at room temperature for 1 hour. The reaction was concentrated in vacuo and saturated sodium bicarbonate solution carefully added. The solid was then filtered and washed with more saturated sodium bicarbonate solution (100 ml) to give the desired compound in suitably clean form to be used without any further purification.

73a: NRR'=morpholino: m/z (LC-MSW, ESP): 251 [M+H]$^+$, R/T=2.75 mins

(iv) 2-(N-Methyl-hydrazino)-pyrido[2,3-d]pyrimidin-4-ylamine derivatives (74)

To a flask charged with isopropyl alcohol (10 ml) was added the appropriate 2-Chloropyrido[2,3-d]pyrimidin-4-ylamine derivative (1 equiv, 0.4 mmol) and methylhydrazine (2 equiv, 0.8 mmol). A reflux condenser was attached and the mixture heated to 50° C. for 16 hours. The mixture was then cooled (0° C.) and the resultant precipitate removed by filtration to give the desired product in suitably clean form to be used without any further purification.

73a: NRR'=morpholino: m/z (LC-MSW, ESP): 261 [M+H]$^+$, R/T=2.31 mins

(v) 2-{N-Methyl-N'-[1-Aryl-methylidene]-hydrazino}-pyrido[2,3-d]pyrimidin-4-ylamine derivatives (75)

To a solution of the appropriate 2-(N-Methyl-hydrazino)-pyrido[2,3-d]pyrimidin-4-ylamine derivative (1 eq, 0.20 mmol) in isopropyl alcohol (5 ml) was added the appropriate aldehyde (2 eq). Acetic acid was then added until pH 4 was reached. The reaction was heated to 80° C. for 1 hour whereupon it was cooled and the resultant precipitate collected. The solid was washed with cold isopropyl alcohol and shown to be the desired product.

All the compounds tested exhibited IC$_{50}$ values less than 15 μM. The following compounds exhibited an IC$_{50}$ less than 1.5 μM: 5a, 5b, 5l, 5n, 5r, 5t, 12a, 12b, 12h, 17l-17c, 27, 29, 36a-36c, 41a, 47a, 50, 53, 59a, 59d-59f, 59i, 59j, 62a, 66a-66h, 69a, 75a, 75b.

REFERENCE LIST

The following documents are all herein incorporated by reference.

1) Brown, et al., *Nature*, 369, 756-758 (1994)
2) Chiu, et al., *Proc Nat Acad Sci*, 91, 12574-12578 (1994)
3) Sabatini, et al., *Cell*, 78, 35-43, (1994)
4) Sabers, et al., *J Biol Chem*, 270, 825-822 (1995)
5) Abraham, *Curr Opin Immunol*, 8, 412-418 (1996)
6) Schmelze and Hall, *Cell*, 103, 253-262 (2000)
7) Burnett, et al., *Proc Natl Acad Sci*, 95, 1432-1437 (1998)
8) Terada, et al., *Proc Natl Acad Sci*, 91,11477-11481 (1994)
9) Jeffries, et al., *EMBO J*, 16, 3693-3704 (1997)
10) Bjornsti and Houghton, *Nat Rev Cancer*, 4, 335-348 (2004)
11) Gingras, et al., *Genes Dev*, 13, 1422-1437 (1999)
12) Gingras, et al., *Genes Dev*, 15, 807-826 (2001)
13) Neuhaus, et al., *Liver Transplantation*, 7, 473-484 (2001)
14) Woods and Marks, *Ann Rev Med*, 55, 169-178 (2004)
15) Dahia, *Endocrine-Related Cancer*, 7, 115-129 (2000)
16) Cristofano and Pandolfi, *Cell*, 100, 387-390 (2000)
17) Samuels, et al., *Science*, 304, 554 (2004)
18) Huang and Houghton, *Curr Opin Pharmacol*, 3, 371-377 (2003)
19) Sawyers, *Cancer Cell*, 4, 343-348 (2003)
20) Huang and Houghton, *Curr Opin in Invest Drugs*, 3, 295-304 (2002)
21) Brunn, et al., *EMBO J*, 15, 5256-5267 (1996)
22) Edinger, et al., *Cancer Res*, 63, 8451-8460, (2003)

| Compound | NRR' | Ar | Purity % | m/z [M + H]$^+$ | RT (mins) |
|---|---|---|---|---|---|
| 75a | *-N(morpholino) | 3,4,5-trihydroxyphenyl (HO, HO, OH) | 99 | 396.9 | 3.03 |
| 75b | *-N(morpholino) | 3,5-dimethoxy-4-hydroxyphenyl | 79 | 424.9 | 3.22 |

Example 16

Biological Assay

For mTOR enzyme activity assays, mTOR protein was isolated from HeLa cell cytoplasmic extract by immunoprecipitation, and activity determined essentially as described previously using recombinant PHAS-1 as a substrate (ref. 21).

23) Lawrence, et al., *Curr Top Microbiol Immunol*, 279, 199-213 (2004)
24) Eshleman, et al., *Cancer Res*, 62, 7291-7297 (2002)
25) Berge, et al., *J. Pharm. Sci.*, 66, 1-19 (1977).
26) Green, T. and Wuts, P., "Protective Groups in Organic Synthesis", 3rd Edition, John Wiley and Sons (1999)
27) "Handbook of Pharmaceutical Additives", 2nd Edition (eds. M. Ash and I. Ash), 2001 (Synapse Information Resources, Inc., Endicott, N.Y., USA),

The invention claimed is:

1. A compound of formula I:

A-B—C    (I)

and isomers and salts thereof
wherein:
B is selected from the group consisting of:

[structures of thiophene and furan with A and C substituents]

A is:

[benzene ring with R^{A2}, R^{A3}, R^{A4}, R^{A5}, R^{A6} and B substituents]

$R^{A3}$ and $R^{A5}$ are independently selected from halo, $OR^O$ and $R^{AC}$;

$R^{A4}$ is selected from H, $OR^O$, $CH_2OH$, $CO_2H$, $NHSO_2Me$ and NHCOMe;

$R^{A2}$ and $R^{A6}$ are independently selected from H, halo and $OR^O$;

or $R^{A3}$ and $R^{A4}$ together with the carbon atoms to which they are attached, or $R^{A2}$ and $R^{A3}$ together with the carbon atoms to which they are attached, may form a $C_{5-6}$ heterocylic or heteroaromatic ring, containing at least one nitrogen ring atom;

where 1, 2, or 3 of $R^{A2}$ to $R^{A6}$ are not H;

C is:

[6-membered ring with X, Y, Z, B, $R^{C3}$, $R^{C5}$ substituents]

where X is selected from N and CH, Y is selected from N and CH, and Z is selected from N and $CR^{C6}$ provided that two of X, Y and Z are N;

$R^{C3}$ is selected from H, halo and an optionally substituted N-containing $C_{5-7}$ heterocyclic group;

$R^{C5}$ is a group selected from:

[structures: morpholino, homomorpholino (7-membered), pyrrolidinyl-$CH_2OR^O$, piperidinyl-$OR^O$ (3-position), piperidinyl-$OR^O$ (4-position), and pyrrolidinyl-$OR^O$]

which group may be optionally substituted by one or two $C_{1-4}$ alkyl groups or a carboxy group;

$R^{C6}$ is H;
or, when X and Y are N, $R^{C5}$ and $R^{C6}$ (when Z is $CR^{C6}$) together with the carbon atoms to which they are attached may form a fused $C_6$ aromatic ring selected from the group consisting of:

[three fused ring structures with $R^{C5}$, $R^{C6}$ and MeO/OMe substituents]

$R^O$ is H or Me; and
$R^{AC}$ is H or $C_{1-4}$ alkyl.

2. The compound according to claim 1, wherein $R^{AC}$ is methyl.

3. The compound according to claim 1, wherein $R^{A2}$ and $R^{A6}$ are selected from H and $OR^O$.

4. The compound according to claim 1, wherein $R^{A4}$ is $OR^O$.

5. The compound according to claim 1, wherein $R^{C3}$ is selected from morpholino, thiomorpholino, piperadinyl, piperazinyl, homopiperazinyl and pyrrolidinyl.

6. The compound according to claim 1, wherein $R^{C5}$ is morpholino.

7. A pharmaceutical composition comprising a compound of formula I:

A-B—C    (I)

and a pharmaceutically acceptable carrier or diluent, wherein:
B is selected from the group consisting of:

[structures of thiophene and furan with A and C substituents]

A is:

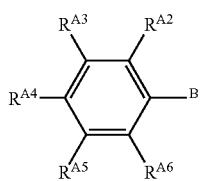

$R^{A3}$ and $R^{A5}$ are independently selected from halo, $OR^O$ and $R^{AC}$;

$R^{A4}$ is selected from H, $OR^O$, $CH_2OH$, $CO_2H$, $NHSO_2Me$ and NHCOMe;

$R^{A2}$ and $R^{A6}$ are independently selected from H, halo and $OR^O$;

or $R^{A3}$ and $R^{A4}$ together with the carbon atoms to which they are attached, or $R^{A2}$ and $R^{A3}$ together with the carbon atoms to which they are attached, may form a $C_{5-6}$ heterocylic or heteroaromatic ring, containing at least one nitrogen ring atom;

where 1, 2, or 3 of $R^{A2}$ to $R^{A6}$ are not H;

C is:

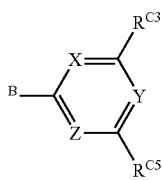

where X is selected from N and CH, Y is selected from N and CH, and Z is selected from N and $CR^{C6}$ provided that two of X, Y, and Z are N;

$R^{C3}$ is selected from H, halo and an optionally substituted N-containing $C_{5-7}$ heterocyclic group;

$R^{C5}$ is a group selected from:

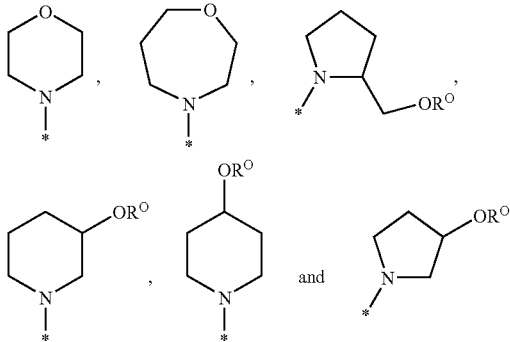

which group may be optionally substituted by one or two $C_{1-4}$ alkyl groups or a carboxy group;

$R^{C6}$ is H;

or, when X and Y are N, $R^{C5}$ and $R^{C6}$ (when Z is $CR^{C6}$) together with the carbon atoms to which they are attached may form a fused $C_6$ aromatic ring selected from the group consisting of:

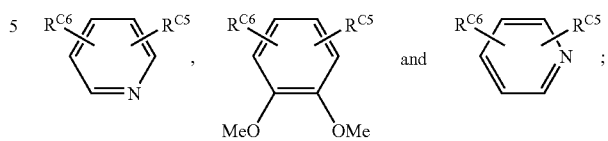

$R^O$ is H or Me; and
$R^{AC}$ is H or $C_{1-4}$ alkyl.

8. The composition according to claim 7, wherein $R^{AC}$ is methyl.

9. The composition according to claim 7, wherein $R^{A2}$ and $R^{A6}$ are selected from H and $OR^O$.

10. The composition according to claim 7, wherein $R^{A4}$ is $OR^O$.

11. The composition according to claim 7, wherein $R^{C3}$ is selected from morpholino, thiomorpholino, piperadinyl, piperazinyl, homopiperazinyl and pyrrolidinyl.

12. The composition according to claim 7, wherein $R^{C5}$ is morpholino.

13. The compound according to claim 1
wherein:

B is

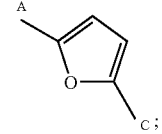

A is selected from:

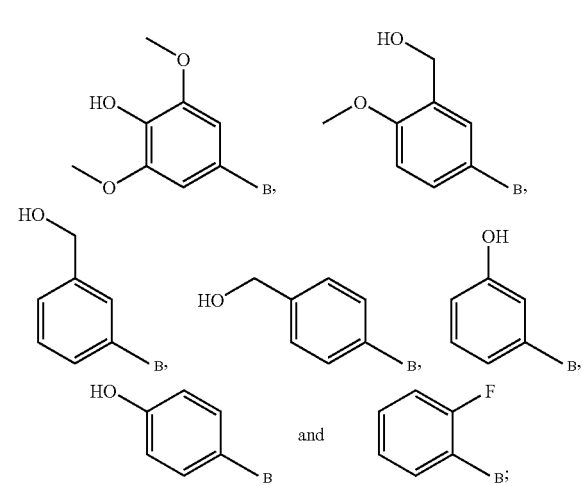

C is:

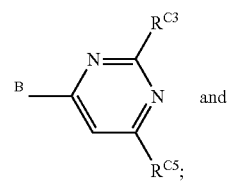

$R^{C3}$ and $R^{C5}$ are both
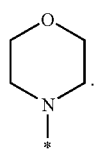
14. The composition according to claim 7 wherein:
B is
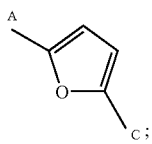
A is selected from:
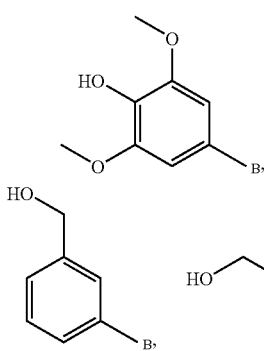 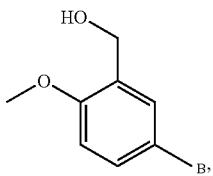
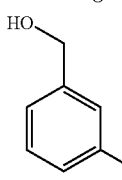 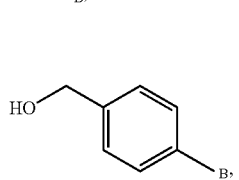
-continued
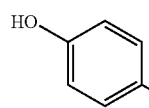 and 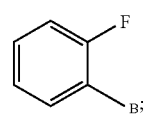
C is:
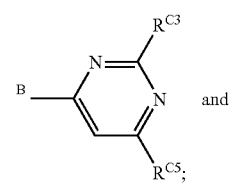 and
$R^{C3}$ and $R^{C5}$ are both
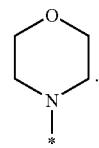
* * * * *